(12) United States Patent
Carson et al.

(10) Patent No.: US 9,622,907 B2
(45) Date of Patent: Apr. 18, 2017

(54) COOLING MEDICAL PAD

(71) Applicant: Medivance Incorporated, Louisville, CO (US)

(72) Inventors: Gary A. Carson, Golden, CO (US); Michael R. Hoglund, Mead, CO (US); Marc E. Voorhees, Arvada, CO (US)

(73) Assignee: Medivance Incorporated, Louisville, CO (US)

( * ) Notice: Subject to any disclaimer, the term of this patent is extended or adjusted under 35 U.S.C. 154(b) by 1140 days.

(21) Appl. No.: 13/662,026

(22) Filed: Oct. 26, 2012

(65) Prior Publication Data

US 2013/0116760 A1     May 9, 2013

Related U.S. Application Data

(63) Continuation-in-part of application No. 13/230,663, filed on Sep. 12, 2011.

(60) Provisional application No. 61/389,056, filed on Oct. 1, 2010, provisional application No. 61/381,840, filed on Sep. 10, 2010.

(51) Int. Cl.
| | |
|---|---|
| *A61F 7/00* | (2006.01) |
| *A61F 7/08* | (2006.01) |
| *A61F 7/10* | (2006.01) |
| *A61F 7/02* | (2006.01) |

(52) U.S. Cl.
CPC ........ *A61F 7/10* (2013.01); *A61F 2007/0056* (2013.01); *A61F 2007/0219* (2013.01); *A61F 2007/0226* (2013.01); *A61F 2007/0247* (2013.01); *A61F 2007/0268* (2013.01)

(58) Field of Classification Search
CPC ................ A61F 7/10; A61F 2007/0219; A61F 2007/0247; A61F 2007/0244; A61F 2007/0246; A61F 2007/0056
See application file for complete search history.

(56) References Cited

U.S. PATENT DOCUMENTS

| | | | |
|---|---|---|---|
| 2,250,325 | A | 7/1941 | Barnes |
| 2,595,328 | A | 5/1952 | Bowen |

(Continued)

FOREIGN PATENT DOCUMENTS

| | | |
|---|---|---|
| JP | 2007029638 A | 2/2007 |
| TW | EP2204150 A1 | 7/2010 |

(Continued)

OTHER PUBLICATIONS

Hyperphysicis, "Thermal Conductivity", available Jul. 31, 2010, https://web.archive.org/web/20100731025127/http://hyperphysics.phy-astr.gus.edu/hbase/tables.thrcn.html Jul. 31, 2010.

(Continued)

*Primary Examiner* — Kaitlyn Smith
(74) *Attorney, Agent, or Firm* — Marsh Fischmann & Breyfogle LLP

(57) ABSTRACT

A medical pad has multiple layers. A first layer is for containing a first thermal-exchange fluid circulatable therethrough, with the medical pad being operable for thermal exchange between the first thermal-exchange fluid and a patient through a first side of the first layer. A second layer of the medical pad is interconnected to a second side of the first layer, opposite to the first side of the first layer. The second layer encloses a second thermal-exchange fluid that may have a freezing point of 0° C. or less. The medical pad is operable for thermal exchange between the second thermal-exchange fluid and the patient.

35 Claims, 25 Drawing Sheets

(56) References Cited

U.S. PATENT DOCUMENTS

| | | |
|---|---|---|
| 2,602,302 A | 7/1952 | Poux |
| 2,726,658 A | 12/1955 | Chessey |
| 3,075,529 A | 1/1963 | Young |
| 3,091,242 A | 5/1963 | Johnson, Jr. et al. |
| 3,212,286 A | 10/1965 | Curtis |
| 3,506,013 A | 4/1970 | Zdenek |
| 3,734,293 A | 5/1973 | Biskis |
| 3,830,676 A | 8/1974 | Elkins |
| 3,867,939 A | 2/1975 | Moore et al. |
| 3,900,035 A | 8/1975 | Welch et al. |
| 3,927,671 A | 12/1975 | Chittenden et al. |
| 3,995,621 A | 12/1976 | Fletcher et al. |
| 4,092,982 A | 6/1978 | Salem |
| 4,108,146 A | 8/1978 | Golden |
| 4,114,620 A | 9/1978 | Moore et al. |
| 4,118,946 A | 10/1978 | Tubin |
| 4,149,541 A | 4/1979 | Gammons et al. |
| 4,154,245 A | 5/1979 | Daily |
| 4,161,210 A | 7/1979 | Reid et al. |
| 4,195,631 A | 4/1980 | Baucom |
| 4,311,022 A | 1/1982 | Hall |
| 4,444,727 A | 4/1984 | Yanagihara et al. |
| 4,508,123 A | 4/1985 | Wyatt et al. |
| 4,580,408 A | 4/1986 | Stuebner |
| 4,753,241 A | 6/1988 | Brannigan et al. |
| 4,834,705 A | 5/1989 | Vaillancourt |
| 4,846,176 A | 7/1989 | Golden |
| 4,886,063 A | 12/1989 | Crews |
| 4,908,248 A | 3/1990 | Nakashima et al. |
| 4,919,134 A | 4/1990 | Streeter |
| 4,962,761 A | 10/1990 | Golden |
| 4,981,135 A | 1/1991 | Hardy |
| 4,989,607 A | 2/1991 | Keusch et al. |
| 5,000,252 A | 3/1991 | Faghri |
| 5,005,374 A | 4/1991 | Spitler |
| 5,050,596 A | 9/1991 | Walasek et al. |
| 5,062,414 A | 11/1991 | Grim |
| 5,072,875 A | 12/1991 | Zacoi |
| 5,097,829 A | 3/1992 | Quisenberry |
| 5,111,668 A | 5/1992 | Parrish et al. |
| 5,113,666 A | 5/1992 | Parrish et al. |
| 5,133,348 A | 7/1992 | Mayn |
| 5,146,625 A | 9/1992 | Steele et al. |
| 5,190,032 A | 3/1993 | Zacoi |
| 5,265,669 A | 11/1993 | Schneider |
| 5,268,022 A | 12/1993 | Garrett et al. |
| 5,289,695 A | 3/1994 | Parrish et al. |
| 5,304,213 A | 4/1994 | Berke et al. |
| 5,304,216 A | 4/1994 | Wallace |
| 5,383,919 A | 1/1995 | Kelly et al. |
| 5,393,462 A | 2/1995 | Avery |
| 5,405,366 A | 4/1995 | Fox et al. |
| 5,407,421 A | 4/1995 | Goldsmith |
| 5,409,500 A | 4/1995 | Dyrek |
| 5,411,541 A | 5/1995 | Bell et al. |
| 5,423,751 A | 6/1995 | Harrison et al. |
| 5,456,701 A | 10/1995 | Stout |
| 5,466,250 A | 11/1995 | Johnson, Jr. et al. |
| 5,470,353 A | 11/1995 | Jensen |
| 5,484,448 A | 1/1996 | Steele et al. |
| 5,486,207 A | 1/1996 | Mahawili |
| 5,514,169 A | 5/1996 | Dickerhoff et al. |
| 5,545,194 A | 8/1996 | Augustine |
| 5,605,144 A | 2/1997 | Simmons et al. |
| 5,609,620 A | 3/1997 | Daily |
| 5,620,482 A | 4/1997 | Augustine et al. |
| 5,624,477 A | 4/1997 | Armond |
| 5,634,940 A | 6/1997 | Panyard |
| 5,640,728 A | 6/1997 | Graebe |
| 5,658,325 A | 8/1997 | Augustine |
| 5,662,695 A | 9/1997 | Mason et al. |
| 5,683,439 A | 11/1997 | Jensen |
| 5,720,774 A | 2/1998 | Glucksman |
| 5,733,318 A | 3/1998 | Augustine |
| 5,755,755 A | 5/1998 | Panyard |
| 5,785,716 A | 7/1998 | Bayron et al. |
| 5,806,335 A | 9/1998 | Herbert et al. |
| 5,824,025 A | 10/1998 | Augustine |
| 5,837,002 A | 11/1998 | Augustine et al. |
| 5,840,080 A | 11/1998 | Der Ovanesian |
| 5,843,145 A | 12/1998 | Brink |
| 5,887,437 A | 3/1999 | Maxim |
| 5,913,849 A | 6/1999 | Sundstrom et al. |
| 5,989,285 A | 11/1999 | DeVilbiss et al. |
| 6,010,528 A | 1/2000 | Augustine et al. |
| 6,019,783 A | 2/2000 | Philips et al. |
| 6,030,412 A | 2/2000 | Klatz et al. |
| 6,047,106 A | 4/2000 | Salyer |
| 6,074,415 A | 6/2000 | Der Ovanesian |
| 6,083,256 A | 7/2000 | Der Ovanesian |
| 6,083,418 A | 7/2000 | Czarnecki et al. |
| 6,117,164 A | 9/2000 | Gildersleeve et al. |
| 6,176,870 B1 | 1/2001 | Augustine |
| 6,185,744 B1 | 2/2001 | Poholski |
| 6,189,149 B1 | 2/2001 | Allen |
| 6,197,045 B1 | 3/2001 | Carson |
| 6,238,427 B1 | 5/2001 | Matta |
| 6,257,011 B1 | 7/2001 | Siman-Tov et al. |
| 6,290,716 B1 | 9/2001 | Augustine |
| 6,349,560 B1 | 2/2002 | Maier-Laxhuber et al. |
| 6,364,937 B1 | 4/2002 | McMahon |
| 6,371,976 B1 | 4/2002 | Vrzalik et al. |
| 6,375,674 B1 | 4/2002 | Carson |
| 6,389,839 B1 | 5/2002 | Sabin |
| 6,436,130 B1 | 8/2002 | Philips et al. |
| 6,454,792 B1 | 9/2002 | Noda et al. |
| 6,461,379 B1 | 10/2002 | Carson et al. |
| 6,463,212 B1 | 10/2002 | Salyer |
| 6,503,297 B1 | 1/2003 | Lu et al. |
| 6,508,831 B1 | 1/2003 | Kushnir |
| 6,508,859 B1 | 1/2003 | Zia et al. |
| 6,511,501 B1 | 1/2003 | Augustine et al. |
| 6,511,502 B2 | 1/2003 | Fletcher |
| 6,559,096 B1 | 5/2003 | Smith et al. |
| 6,584,797 B1 | 7/2003 | Smith et al. |
| 6,591,630 B2 | 7/2003 | Smith et al. |
| 6,601,404 B1 | 8/2003 | Roderick |
| 6,620,187 B2 | 9/2003 | Carson et al. |
| 6,645,232 B2 | 11/2003 | Carson |
| 6,653,607 B2 | 11/2003 | Ellis et al. |
| 6,669,715 B2 | 12/2003 | Hoglund et al. |
| 6,682,525 B2 | 1/2004 | Lalonde et al. |
| 6,688,132 B2 | 2/2004 | Smith et al. |
| 6,692,518 B2 | 2/2004 | Carson |
| 6,701,724 B2 | 3/2004 | Smith et al. |
| 6,743,250 B2 | 6/2004 | Renfro |
| 6,755,801 B2 | 6/2004 | Utterberg et al. |
| 6,755,852 B2 | 6/2004 | Lachenbruch et al. |
| 6,770,848 B2 | 8/2004 | Haas et al. |
| 6,800,087 B2 | 10/2004 | Papay et al. |
| 6,802,855 B2 | 10/2004 | Ellingboe et al. |
| 6,818,012 B2 | 11/2004 | Ellingboe |
| 6,858,068 B2 | 2/2005 | Smith et al. |
| 6,878,156 B1 | 4/2005 | Noda |
| 6,893,453 B2 | 5/2005 | Agarwal et al. |
| 6,904,956 B2 | 6/2005 | Noel |
| 6,909,074 B1 | 6/2005 | Bradley |
| 6,931,875 B1 | 8/2005 | Allen et al. |
| 6,960,243 B1 | 11/2005 | Smith et al. |
| 6,968,711 B2 | 11/2005 | Smith et al. |
| 6,969,399 B2 | 11/2005 | Schock et al. |
| 7,008,445 B2 | 3/2006 | Lennox |
| 7,022,099 B2 | 4/2006 | Litzie et al. |
| 7,052,509 B2 | 5/2006 | Lennox et al. |
| 7,055,575 B2 | 6/2006 | Noel |
| 7,056,335 B2 | 6/2006 | Agarwal et al. |
| 7,063,718 B2 | 6/2006 | Dobak, III |
| 7,077,858 B2 | 7/2006 | Fletcher et al. |
| 7,097,657 B2 | 8/2006 | Noda et al. |
| 7,101,389 B1 | 9/2006 | Augustine et al. |
| 7,172,586 B1 | 2/2007 | Dae et al. |
| 7,240,720 B2 | 7/2007 | Noel |
| 7,303,554 B2 | 12/2007 | Lalonde et al. |
| 7,303,579 B2 | 12/2007 | Schock et al. |

(56) References Cited

U.S. PATENT DOCUMENTS

| | | |
|---|---|---|
| 7,338,516 B2 | 3/2008 | Quincy, III et al. |
| 7,377,935 B2 | 5/2008 | Schock et al. |
| 7,507,250 B2 | 3/2009 | Lennox |
| 7,517,360 B2 | 4/2009 | Frey et al. |
| RE40,815 E | 6/2009 | Kudaravalli et al. |
| 7,547,320 B2 | 6/2009 | Schook et al. |
| RE40,868 E | 8/2009 | Ryba et al. |
| 7,621,944 B2 | 11/2009 | Wilson et al. |
| 7,621,945 B2 | 11/2009 | Lennox et al. |
| 7,666,213 B2 | 2/2010 | Freedman, Jr. et al. |
| 7,678,716 B2 | 3/2010 | Yahiaoui et al. |
| 7,686,840 B2 | 3/2010 | Quincy, III et al. |
| 7,727,228 B2 | 6/2010 | Abboud et al. |
| 7,731,739 B2 | 6/2010 | Schock et al. |
| 7,744,640 B1 | 6/2010 | Faries, Jr. et al. |
| 7,763,061 B2 | 7/2010 | Schorr et al. |
| 7,771,461 B2 | 8/2010 | Schock et al. |
| 7,799,063 B2 | 9/2010 | Ingram et al. |
| 7,827,815 B2 | 11/2010 | Carson et al. |
| 7,896,910 B2 | 3/2011 | Schirrmacher et al. |
| 8,047,010 B2 | 11/2011 | Carson et al. |
| 8,052,624 B2 | 11/2011 | Buchanan et al. |
| 8,187,697 B2 | 5/2012 | Quincy, III et al. |
| 3,283,602 A1 | 10/2012 | Augustine et al. |
| 8,597,217 B2 | 12/2013 | Lowe et al. |
| 8,778,119 B2 | 7/2014 | Starr et al. |
| 9,078,742 B2 | 7/2015 | Quincy, III et al. |
| 9,089,462 B1 | 7/2015 | Lafleche |
| 2003/0109911 A1 | 6/2003 | Lachenbruch et al. |
| 2003/0149461 A1 | 8/2003 | Johnson |
| 2003/0150232 A1 | 8/2003 | Brudnicki |
| 2004/0064170 A1 | 4/2004 | Radons et al. |
| 2004/0082886 A1 | 4/2004 | Timpson |
| 2004/0243122 A1 | 12/2004 | Auth et al. |
| 2005/0060012 A1 | 3/2005 | Voorhees et al. |
| 2005/0096714 A1 | 5/2005 | Freedman et al. |
| 2005/0187502 A1 | 8/2005 | Krempel et al. |
| 2005/0244629 A1 | 11/2005 | Usui et al. |
| 2005/0288749 A1 | 12/2005 | Lachenbruch |
| 2006/0030916 A1 | 2/2006 | Lennox |
| 2006/0036304 A1 | 2/2006 | Cordani et al. |
| 2006/0074469 A1 | 4/2006 | Lennox et al. |
| 2006/0124141 A1 | 6/2006 | Dobak, III |
| 2006/0136023 A1 | 6/2006 | Dobak, III |
| 2006/0161232 A1 | 7/2006 | Kasza et al. |
| 2006/0247744 A1 | 11/2006 | Nest et al. |
| 2006/0276089 A1 | 12/2006 | Amarasinghe et al. |
| 2006/0287697 A1 | 12/2006 | Lennox |
| 2007/0043409 A1 | 2/2007 | Brian, III et al. |
| 2007/0049997 A1 | 3/2007 | Fields et al. |
| 2007/0054122 A1 | 3/2007 | Paisner et al. |
| 2007/0068931 A1 | 3/2007 | Augustine et al. |
| 2007/0225782 A1 | 9/2007 | Taylor |
| 2007/0270925 A1 | 11/2007 | Levinson |
| 2008/0027523 A1 | 1/2008 | Behringer et al. |
| 2008/0147152 A1 | 6/2008 | Quincy et al. |
| 2008/0249524 A1 | 10/2008 | Dunning |
| 2008/0255644 A1 | 10/2008 | Carson |
| 2008/0275534 A1 | 11/2008 | Noel |
| 2009/0088825 A1 | 4/2009 | Ota |
| 2009/0099629 A1 | 4/2009 | Carson et al. |
| 2009/0131835 A1 | 5/2009 | Voorhees et al. |
| 2009/0177184 A1 | 7/2009 | Christensen et al. |
| 2009/0287283 A1 | 11/2009 | Biser et al. |
| 2009/0312823 A1 | 12/2009 | Patience et al. |
| 2009/0326619 A1 | 12/2009 | Kagan |
| 2010/0016933 A1 | 1/2010 | Chen et al. |
| 2010/0168825 A1 | 7/2010 | Barbknecht |
| 2010/0198122 A1 | 8/2010 | Freund |
| 2010/0198320 A1 | 8/2010 | Pierre |
| 2011/0029051 A1 | 2/2011 | Ross |
| 2011/0306972 A1 | 12/2011 | Widenhouse et al. |
| 2011/0308781 A1 | 12/2011 | O'Riordan et al. |
| 2011/0313497 A1 | 12/2011 | McFarlane |
| 2012/0046720 A1 | 2/2012 | Ishizaki |
| 2012/0065715 A1 | 3/2012 | Carson |
| 2012/0191035 A1 | 7/2012 | Stephan |
| 2012/0220960 A1 | 8/2012 | Ruland |
| 2013/0116760 A1 | 5/2013 | Carson et al. |
| 2014/0214138 A1 | 7/2014 | Voorhees et al. |
| 2014/0277301 A1 | 9/2014 | Varga et al. |
| 2015/0373781 A1 | 12/2015 | Augustine et al. |

FOREIGN PATENT DOCUMENTS

| | | |
|---|---|---|
| WO | PCT/IL99/00059 A1 | 9/1999 |
| WO | PCT/US03/010311 A2 | 10/2003 |

OTHER PUBLICATIONS

Advantage Engineering, "Proper Use of Inhibited Propylene Glycol", Jun. 12, 2001, http://www.ttequip.com/knowledgelibrary/Proper%20Use%20Of%20Inhibited%20Propylene%20Glycol.pdf Jun. 12, 2001.

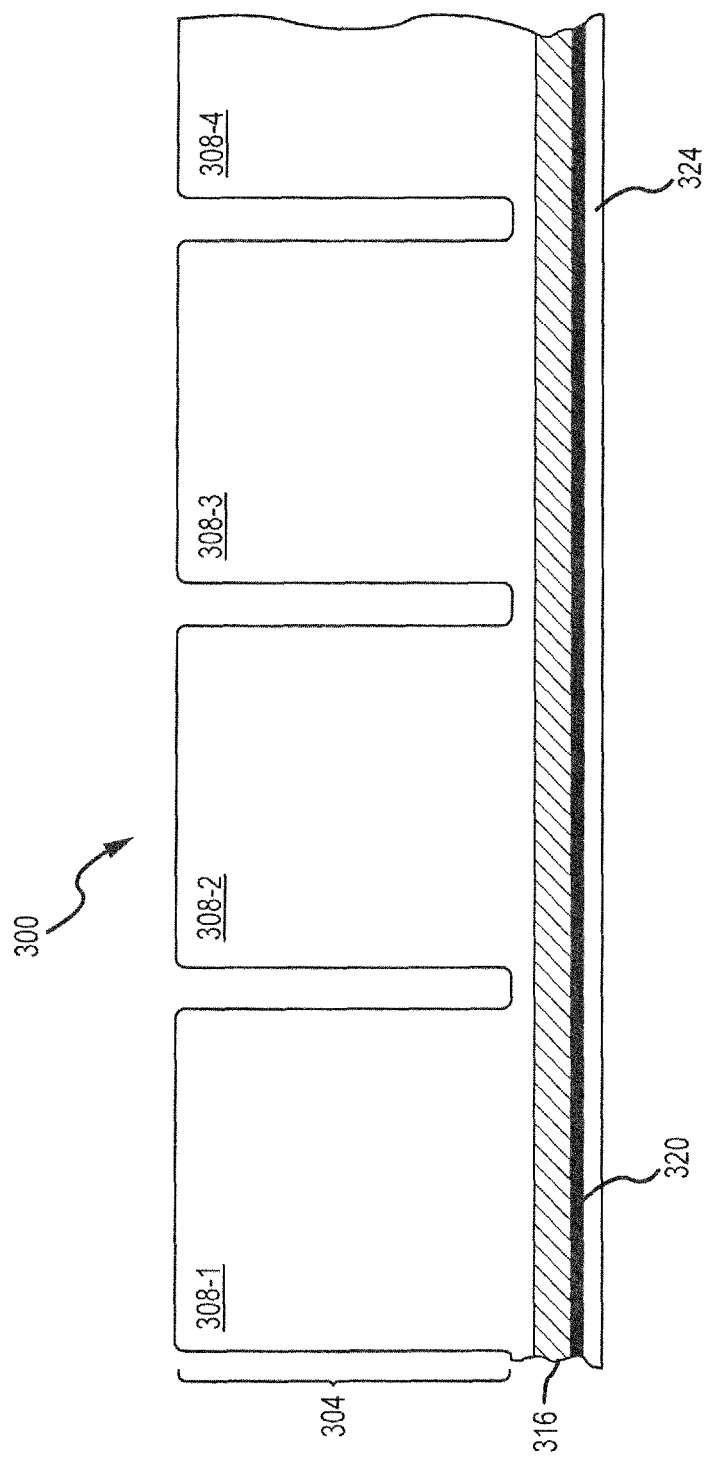

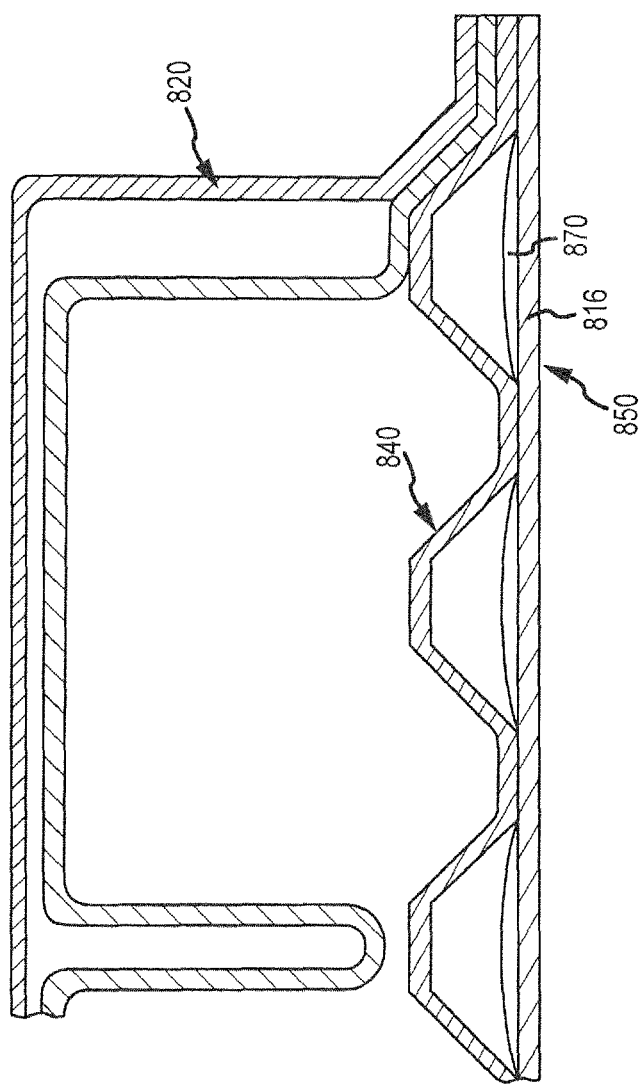

COOLING MEDICAL PAD

RELATED APPLICATIONS

This application is a continuation-in-part of U.S. patent application Ser. No. 13/230,663, filed Sep. 12, 2011, entitled "COOLING MEDICAL PAD," which claims priority to U.S. Provisional Patent Application No. 61/389,056, filed Oct. 1, 2010, entitled "COOLING MEDICAL PAD," and U.S. Provisional Patent Application No. 61/381,840, filed Sep. 10, 2010, all of which applications are incorporated herein by reference in their entirety.

FIELD OF THE INVENTION

The present invention relates to cooling medical patients. More specifically, this application relates to a cooling pad for treating medical patients benefiting from cooling treatment and to methods for using such a cooling pad.

BACKGROUND OF THE INVENTION

There are a number of medical conditions in which systemic cooling is an effective therapy. For example, rapid systemic cooling of stroke and head-trauma patients has significant therapeutic benefits. Stroke is a major cause of death and neurological disability, but recent research has suggested that even though a stroke victim's brain cells may lose their ability to function during the stroke, they do not necessarily die quickly. Brain damage resulting from a stroke may take hours to reach maximum effect. Neurological damage may be limited and the stroke victim's outcome improved if a cooling neuroprotectant therapy is applied during that timeframe.

Similar possibilities exist with the victims of trauma such as may result from vehicle crashes, falls, and the like. Such trauma may cause brain injury through mechanisms that have overlap with elements in the genesis of neurologic damage in stroke victims. Delayed secondary injury at the cellular level after the initial head trauma event is recognized as a major contributing factor to the ultimate tissue loss that occurs after brain injury.

Cooling therapy has been shown in a number of studies to confer neuroprotection in stroke victims and may hasten neurologic recovery. Such cooling therapy may be applied with the use of a medical cooling pad that is placed on the patient. For example, the pad might be placed on the patient's torso and fluid such as water or air circulated through the pad. Thermal energy is then exchanged between the patient and the circulated fluid so that when the temperature of the fluid is lower than the desired temperature of the patient, the patient is cooled.

SUMMARY OF THE INVENTION

Embodiments of the invention provide a medical pad that comprises a plurality of layers. A first layer of the medical pad is for containing a first thermal-exchange fluid circulatable therethrough (e.g., cooled fluid circulated via an interconnected pump/heat exchange unit). The medical pad is selectively positionable to contact a patient on a first side thereof, and is operable for thermal exchange between the circulatable first thermal-exchange fluid and a patient through a first side of the first layer and the first side of the medical pad. A second layer of the medical pad may be disposed on a second side of the first layer, opposite to the first side of the first layer. The second layer encloses a second thermal-exchange fluid.

The medical pad is operable for thermal exchange between the second thermal-exchange fluid and the patient through the first side of the medical pad. In some approaches the second thermal-exchange fluid may comprise a liquid having a freezing point of 0° C. or less. In turn, in such approaches, the second thermal-exchange fluid contained in the second layer may be chilled, e.g., to at least a semi-frozen state, prior to use. Additionally, in such approaches, the second thermal-exchange fluid may comprise liquid in a gel form. For example, a gel material comprising a water/polymer matrix may be utilized. In some implementations, shape-holding gels may be utilized.

The medical pad may be configured for different levels of thermal communication with the first and second thermal-exchange fluids in different embodiments. In some embodiments, for example, greater than 30% of an area of the medical pad in contact with the patient is in thermal communication with the first thermal-exchange fluid (e.g., located adjacent thereto), and in a specific embodiment, approximately 50% of the area of the medical pad in contact with the patient is in thermal communication with the first thermal-exchange fluid (e.g., located adjacent thereto). Similarly, in other embodiments, greater than 30% of an area of the medical pad in contact with the patient is in thermal communication with the second thermal-exchange fluid (e.g., located adjacent thereto), and in a specific embodiment, approximately 50% of the area of the medical pad in contact with the patient is in thermal communication with the second thermal-exchange fluid (e.g., located adjacent thereto).

In one embodiment, approximately 50% of the area of the medical pad in contact with the patient is in thermal communication with the first thermal-exchange fluid (e.g., located adjacent thereof) and approximately 50% of the area of the medical pad in contact with the patient is in thermal communication with the second thermal-exchange fluid (e.g., located adjacent thereto).

The second layer may extend across at least a majority of a lateral extent of the first layer. Further, the second layer may comprise a plurality of chambers. In some such embodiments, the plurality of chambers may each enclose a corresponding different portion of the second thermal-exchange fluid therewithin. In some embodiments, at least a portion of each of the plurality of enclosed chambers may be located laterally adjacent (e.g., side-by-side) with corresponding first thermal-exchange fluid containment portions, e.g., fluid flow channels, of the first layer.

Each of the plurality of chambers may project away from the second side of the first layer with indentations defined therebetween. For instance, the plurality of chambers may, in one embodiment, define a waffle-shaped configuration. The provision of indentations between adjacent chambers (e.g., laterally and/or longitudinally extending indentations), together with the utilization of pliable materials to define the first and second layers, allows for a degree of pivotal, or hinge-like movement, about such indentations. Such feature facilitates medical contact with a patient and is particularly advantageous when the second thermal-exchange fluid is in a solid or semi-solid state (e.g., ice).

An adhesive surface may be disposed on the first side of the first layer and adapted for releasable adhesive contact with skin of a patient. In certain embodiments, the adhesive surface extends across at least a majority of a lateral extent of the first layer. In such embodiments, the first and second layers may also be adapted for conformal contact between the adhesive surface and the skin of the patient. For example, as indicated above, the first and second layers may be defined by pliable materials.

Ports may be fluidly interconnected to the first layer for selective interconnection to a separate pump/heat exchanger unit provided for circulation of the first thermal-exchange fluid. In such cases, a first port is fluidly interconnected to the first layer for circulating the first thermal-exchange fluid into the first layer and a second port is fluidly interconnected to the first layer for circulating the first thermal-exchange fluid out of the first layer.

Embodiments of the invention may also comprise different thermal properties for the thermal-exchange fluids. For example, at least one of the first thermal-exchange fluid or the second thermal-exchange fluid may have a thermal conductivity that exceeds 5.0 W/mK, that exceeds 10.0 W/mK, that exceeds 50.0 W/mK, that exceeds 100.0 W/mK, or that exceeds 250 W/mK in various embodiments. The at least one of the first thermal-exchange fluid or the second thermal-exchange fluid may comprise a liquid containing a material having a thermal conductivity that exceeds a thermal conductivity of the liquid by at least a factor of 10, a factor of 50, a factor of 100, a factor of 500, or a factor of 1000 in various embodiments.

Embodiments of the invention also include methods for contact cooling of a patient and for providing a medical pad for contact cooling. In the former aspect, a medical pad may be positioned on a patient. Thermal energy is transferred as part of a first transferring step between a contained layer of the medical pad and the patient. The contained layer may enclose a first thermal-exchange fluid that is chilled, e.g., to a temperature of 5° C. or less (e.g., frozen water). Thermal energy is also transferred as part of a second transferring step between a circulation layer of the medical pad and the patient by circulating a second thermal-exchange fluid through the circulation layer of the medical pad.

The first transferring step may be performed over greater than 30% of an area of the medical pad in contact with the patient, and in some cases is performed over approximately 50% of an area of the medical pad in contact with the patient. Similarly, the second transferring step may be performed over greater than 30% of an area of the medical pad in contact with the patient, and in some cases is performed over approximately 50% of the area. In one embodiment, the first transferring step is performed over approximately 50% of an area in contact with the patient and the second transferring step is performed over approximately 50% of the area.

The first and second transferring steps may be at least partially offset. For instance, the first transferring step may be initiated at a first location and the second transferring step may be initiated at a second location different from the first location. In such cases, the patient may be moved from the first location to the second location between initiation of the first transferring step and initiation of the second transferring step, such as in an ambulatory vehicle. In some embodiments, at least a portion of the first transferring step is completed during the moving step.

The method may also comprise cooling the medical pad prior to each of the positioning, first transferring, and second transferring steps. In such cases, the first thermal-exchange fluid may be chilled by such cooling to a temperature below at least 5° C. In some approaches, the first thermal-exchange fluid may be chilled to a frozen or semi-frozen state prior to positioning at the pad on a patient.

In some embodiments, the medical pad may be positioned on the patient by adhering the medical pad to skin of a bodily portion of the patient. In such embodiments, a liner may be removed from an adhesive surface of the medical pad, and the adhesive surface of the medical pad may be contacted with the skin of the bodily portion of the patient. The adhesive surface may extend across at least a majority of a lateral extent of the circulation layer. Thermal exchange may occur across the adhesive surface during the first transferring step and during the second transferring step, e.g., without displacing or otherwise repositioning the medical pad relative to the patient.

In some embodiments, the second transferring step comprises fluidly interconnecting the medical pad to a fluid control system. In such embodiments, the second thermal-exchange fluid may be circulated through the circulation layer of the medical pad and the fluid control system.

Another aspect of the invention provides a medical pad that comprises a plurality of layers that are attached at least about their peripheries to form first and second fluid compartments that are adapted to hold first and second thermal-exchange fluids, respectively. Generally, the plurality of layers are formed from sheets of non-permeable materials (e.g., polymeric materials). The medical pad includes an upper sheet layer or containment layer, an intermediate sheet layer and a lower sheet layer/patient interface layer. The intermediate sheet layer has a plurality depressions formed in a top surface that define a corresponding plurality of projections on its bottom surface. A top surface of the lower sheet layer is juxtaposed against the projections on the bottom surface of the intermediate sheet layer. The peripheries of the lower sheet layer and the intermediate sheet layer are connected such that spaces between the projections on the bottom surface of the intermediate sheet layer and the top surface of the lower sheet layer collectively define a fluid circulation layer for containing a first thermal-exchange fluid circulatable therethrough. The upper sheet layer is disposed over a top surface of the intermediate sheet layer and the peripheries of the upper sheet layer and intermediate sheet layer are interconnected to define a fluid containment layer enclosing a second thermal-exchange fluid. The attached peripheries of the lower sheet layer and intermediate sheet layer and the peripheries of the upper sheet layer and intermediate sheet layer may be common peripheries. However, this is not a requirement.

In one arrangement, the connection of the peripheries between the lower sheet layer and the intermediate sheet layer form the only physical interconnection between these layers. That is, the projections on the bottom surface of the intermediate sheet layer are not mechanically connected to mating portions of the lower sheet layer. In another arrangement, some or all of the projections on the bottom surface of the intermediate sheet layer may be attached to corresponding mating portions of the lower sheet layer. Stated otherwise, contacting portions of the intermediate sheet layer and lower sheet layer within their peripheries may be attached in addition to the peripheries. In one specific arrangement, less than all of the contacting portions between these layers are interconnected. For instance, elongated projections or ribs formed on the bottom surface of the intermediate layer, which direct flow through the fluid circulation, may be connected to mating portions of the lower sheet layer. In such an arrangement, the ribs may be attached to the lower sheet layer while other projections on the bottom surface of the intermediate sheet layer contacting lower sheet layer are free of attachment.

The medical pad may be configured for different levels of thermal communication between the lower sheet layer and the fluid circulation and fluid containment layers. In some embodiments, for example, a total area of the projections that contact the lower sheet layer cover at least 30% of the total area of the lower sheet layer. In this regard, the second thermal-exchange fluid disposed in the fluid containment layer and which is in fluid contact with the depressions corresponding to the projections is in contact with at least 30% of the surface area of the lower sheet layer. In other embodiments, the total area of the projections that contact the lower sheet layer cover at least 50% of the total area of the lower sheet layer.

The upper sheet layer may extend across at least a majority of the lateral extent of the intermediate layer. Further, the upper sheet layer may comprise a plurality of chambers. In some such embodiments, the plurality of chambers may each enclose corresponding different portions of the second thermal-exchange fluid therewithin. In other embodiments, one or more of the plurality of chambers may be in fluid communication with one or more adjacent chambers. In some embodiments, at least a portion of each of the plurality of chambers may be located adjacent with corresponding first thermal-exchange fluid containment portions, e.g., flow channels, of the fluid circulation layer. That is, the chambers may overlay portions of the fluid flow channels of the fluid circulation layer.

Each of the plurality of chambers may project away from a top side of the upper layer with indentations defined therebetween. For instance, the plurality of chambers may, in one embodiment, define a waffle-shaped configuration. The provision of indentations between adjacent chambers, together with the utilization of pliable materials to define the layers of the pad, allows for degree of pivotal, or hinge like movement, about such indentations.

In a further arrangement, one or more additional layers may be applied to the medical pad. In one arrangement, a top or insulative layer may be disposed over at least a portion of the top surface of the upper sheet layer. In a further arrangement, the top layer may further include a plurality of corrugations that allow the medical pad to expand or collapse when applied to a non-planar surface (e.g., when the adjacent chambers experience pivotal or hinge-like movement). For example, the top layer may expand or collapse in an accordion-like manner. In a yet further arrangement, the top layer may include one or more recesses that extend across a lateral extent thereof in one or more directions. These recesses may extend below a top surface of the top layer and/or be disposed within the indentations between adjacent chambers of the underlying fluid containment layer. In such an arrangement, the depth of the recess(es) in the top layer may extend below a top surface of the fluid containment layer (e.g., below the top surfaces of the adjacent chambers) into the indentations between adjacent chambers. In one specific arrangement, the recesses may extend to a depth of greater than 20% of the depth of the indentations. In a further arrangement, the recesses may extend to a depth of greater than 30%, greater than 40%, greater than 50%, greater than 60%, greater than 70%, or greater than 80% of the depth of the indentations.

In another arrangement, an adhesive surface may be disposed on a bottom surface of the lower sheet layer that is adapted for releasable adhesive contact with skin of the patient. In such an arrangement, the adhesive layer may be covered by a release sheet that may be removed prior to attaching the pad to a patient.

Ports may be fluidly interconnected to the fluid circulation layer for selective interconnection to a separate pump/heat exchanger unit provided for circulation of the first thermal-exchange fluid. Likewise, one or more ports may be fluidly interconnected to the fluid containment layer for use in introducing the second thermal-exchange fluid into the fluid containment layer.

According to another aspect, a process for manufacturing a medical pad is provided. The process includes placing a lower sheet layer below a bottom surface of an immediate sheet layer having a plurality depressions formed a top surface that define a corresponding plurality of projections on its bottom surface. Such positioning may allow for juxtaposing the top surface of the lower sheet layer against the projections of on the bottom surface of the intermediate sheet layer. The peripheries of the lower sheet layer and immediate sheet layer may be attached or otherwise sealed together to define a fluid circulation layer therebetween. An upper sheet layer may be disposed over top surface of the intermediate sheet layer. Peripheries of the upper sheet layer and lower sheet layer may be attached or otherwise sealed together to define a fluid containment layer there between.

In one arrangement, the peripheries of the lower sheet layer and intermediate sheet layer may be attached prior to placing the upper sheet layer over the intermediate layer. In another arrangement, the lower sheet layer intermediate sheet layer and upper sheet layer may be positioned in a common process and the peripheries of all of these layers may be attached in a common process. For example, these layers may be simultaneously attached about their peripheries in the same attachment process. Likewise, one or more additional layers may be applied to the medical pad for common attachment. For instance, an insulative layer may be disposed over the upper sheet layer.

The process may further include passing or introducing a thermal exchange-fluid into the fluid containment layer. In this regard, a first port in the fluid containment layer may be interconnected to a source of the thermal-exchange fluid. In one arrangement, the thermal-exchange fluid may flow through the fluid containment layer between the first port and a second port, which provides gas pressure relief for gases within the fluid containment layer prior to introduction of the thermal-exchange fluid. In another arrangement, the thermal-exchange fluid may be introduced through a single port. In such an arrangement, it may be desirable to evacuate the fluid containment layer to a predetermined pressure below atmospheric pressure prior to introducing the thermal exchange-fluid into the fluid containment layer where gas pressure relief via a second port is avoided (i.e., no second port is required). The process may further include applying an adhesive to the bottom surface of the lower sheet layer for use in selectively adhering to medical pad to a patient.

According to another aspect, a process is provided for introducing a gel material into a fluid containment compartment or layer of a medical pad. The process includes connecting a vacuum source to a first port of the fluid containment layer of a medical pad where the fluid containment layer is adapted to sealably hold a fluid. Once connected to the port, the fluid containment layer may be evacuated to a predetermined pressure below atmospheric pressure. Once reaching the predetermined pressure below atmospheric pressure, a gel material may be introduced (e.g., flowed) into the fluid containment layer. In one arrangement, the gel may flow through the first port commonly connected to the vacuum source.

In one arrangement, the fluid containment layer is evacuated to a predetermined pressure that is below 100 mmHg. In a further arrangement, the fluid containment layer is evacuated to a predetermined below 10 mmHg.

In one arrangement, introducing the gel material into the fluid containment layer includes pumping the gel material into the containment layer under positive pressure. In any arrangement, to effectively introduce the gel material into the fluid containment layer, a gel material having a viscosity of less than 15,000 centipoise may be utilized. In a further arrangement, a gel having a viscosity of less than 5,000 centipoise may be utilized.

In a further arrangement, where the medical pad includes a second fluid circulation layer that extends across a majority of lateral extent of the fluid containment layer, the process may further include evacuating the fluid circulation layer to the predetermined pressure below atmospheric pressure. In one specific arrangement, evacuation of the fluid containment layer and fluid circulation layer further includes placing the medical pad in a vacuum chamber such that the layers are evacuated simultaneously.

In a further aspect, a process for producing a gel material and introducing the gel material into medical pad is provided. The process includes de-gassing water to provide de-gassed water that inhibits the formation of bubbles at pressures below atmospheric pressure. The de-gassed water is mixed with a gelling agent and cross-linking material to generate a gel material having initial viscosity of less than 15,000 centipoise. Once the gel material is mixed, the process includes evacuating a fluid containment layer of a medical pad to predetermined pressure below atmospheric pressure. Upon achieving the predetermined pressure in the fluid containment layer, the gel material is introduced into the fluid containment layer.

In a further arrangement, the process includes mixing a gelling agent formed of a cellulose gel in a concentration between 0.5% and 3.5% by weight of the resulting gel material with the de-gassed water. In one arrangement, the cellulose gel comprises a carboxmethyl cellulose (CMC) material. In a further arrangement, the CMC material has a high molecular weight between about 250,000-700,000 grams per mol. In a yet further arrangement, the cross-linking material comprises an aluminum acetate material.

Numerous additional features and advantages of the present invention will become apparent to those skilled in the art upon consideration of the embodiment descriptions provided hereinbelow.

BRIEF DESCRIPTION OF THE DRAWINGS

A further understanding of the nature and advantages of the present invention may be realized by reference to the remaining portions of the specification and the drawings wherein like reference numerals are used throughout the several drawings to refer to similar components. In some instances, a sublabel is associated with a reference numeral following a hyphen to denote one of multiple similar components. When reference is made to a reference numeral without specification to an existing sublabel, it is intended to refer to all such multiple similar components.

FIGS. 3A and 3B provide cross-sectional views of medical pads for different embodiments of the invention;

FIG. 9G is another cross sectional view of the medical pad embodiment of FIG. 8;

DETAILED DESCRIPTION

Embodiments of the invention provide a medical pad and methods of contact cooling a patient. The medical pad includes a plurality of layers, at least one of which is a circulation layer for containing a circulatable thermal-exchange fluid that can circulate through the layer and at least one of which is a containment layer that encloses a contained thermal-exchange fluid.

Figure 1:
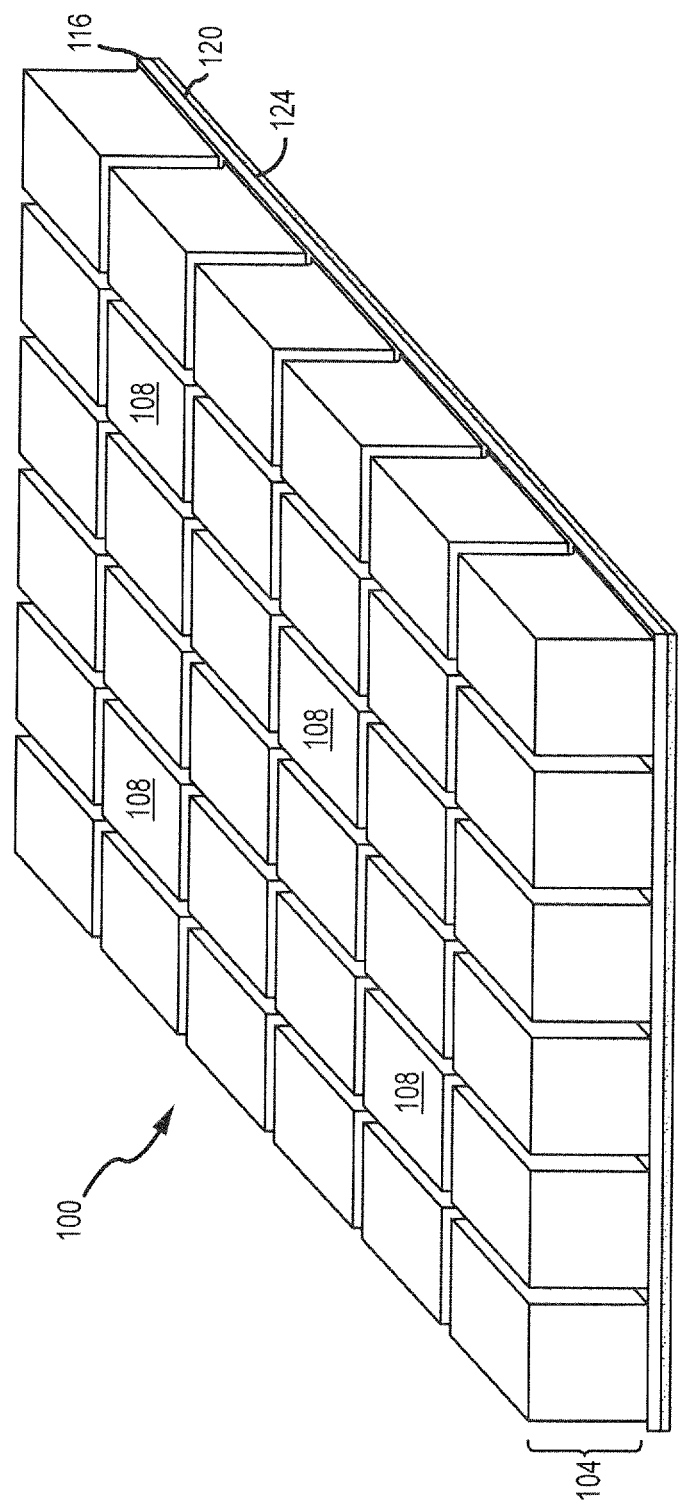
FIG. 1 illustrates a general configuration for a medical pad in accordance with embodiments of the invention.

A general overview of one structure for the medical pad according to embodiments of the invention is provided with FIG. 1, which shows a three-dimensional view of a portion of a medical pad 100. A circulation layer 116 comprises a fluid-containing layer for containing the circulatable thermal-exchange fluid that is capable of absorbing and/or releasing thermal energy. A circulation layer 116 may also comprise a conformable thermally conductive layer for facilitating thermal exchange with a patient.

An adhesive surface 120 may be disposed on a skin-contacting side of the circulation layer 116 for adhering the pad 100 to the skin of a patient. A removable liner 124 may be provided over the adhesive surface 120 to protect the adhesive surface 120 from contamination while the pad 100 is not in use. The removable liner 124 may be selectively removed when the pad 100 is used.

In one approach, the adhesive surface 120 may be provided as a number of downward-facing adhesive strips (e.g., peripheral strips and/or strips extending across the lateral extent of the medical pad), each having a selectively removable release liner 124 exposed thereupon. The adhesive strips may comprise a polyolefin or polyurethane film with hypoallergenic pressure-sensitive acrylate adhesive anchored to the pad 100 with a rubber-based pressure-sensitive adhesive.

In another approach, the adhesive surface 120 may be provided on a conformable, thermally conductive layer. The conformable, thermally conductive layer may comprise a first material, such as a liquid (e.g., water), suspended in a matrix defined by a second material, such as a polymer. In this regard, the liquid may preferably comprise between about 30% to 95% by weight of the total weight of the first and second materials. The adhesive surface and thermal transfer layers may be separately comprised of distinct materials. Alternatively, a thermally conductive layer may be comprised of a hydrogel material having sufficient adhesive properties so as to integrally provide the adhesive surface. In such approaches, the adhesive surface 120 may extend across the entirety or at least a majority of the skin-contacting side of medical pad 100.

A containment layer 104 may be interconnected with a second side of the circulation layer 116 that is opposite the skin-contacting side of the circulation layer 116. The containment layer 104 may include a plurality of chambers 108 which may be individually or collectively enclosed in some embodiments, or which may be enclosed in groups in other embodiments. Each of the chambers 108 may be defined by pliable members that project away from the second side of the circulation layer 110 and may have indentations therebetween as illustrated in the drawing (e.g., thereby defining a waffle-like configuration).

A first thermal-exchange fluid is generally used for circulation through the circulation layer 116 and a second thermal-exchange fluid is generally used for containment in the containment layer 104. As described in further detail below, the first and second thermal-exchange fluids may sometimes be the same fluid, but this is not a requirement of the invention and different thermal-exchange fluids may be used in the circulation and containment layers in different embodiments. In the later regard, in some embodiments, the second thermal-exchange fluid may comprise a liquid of a gel material, e.g., a shape-holding gel material.

Figure 2A:
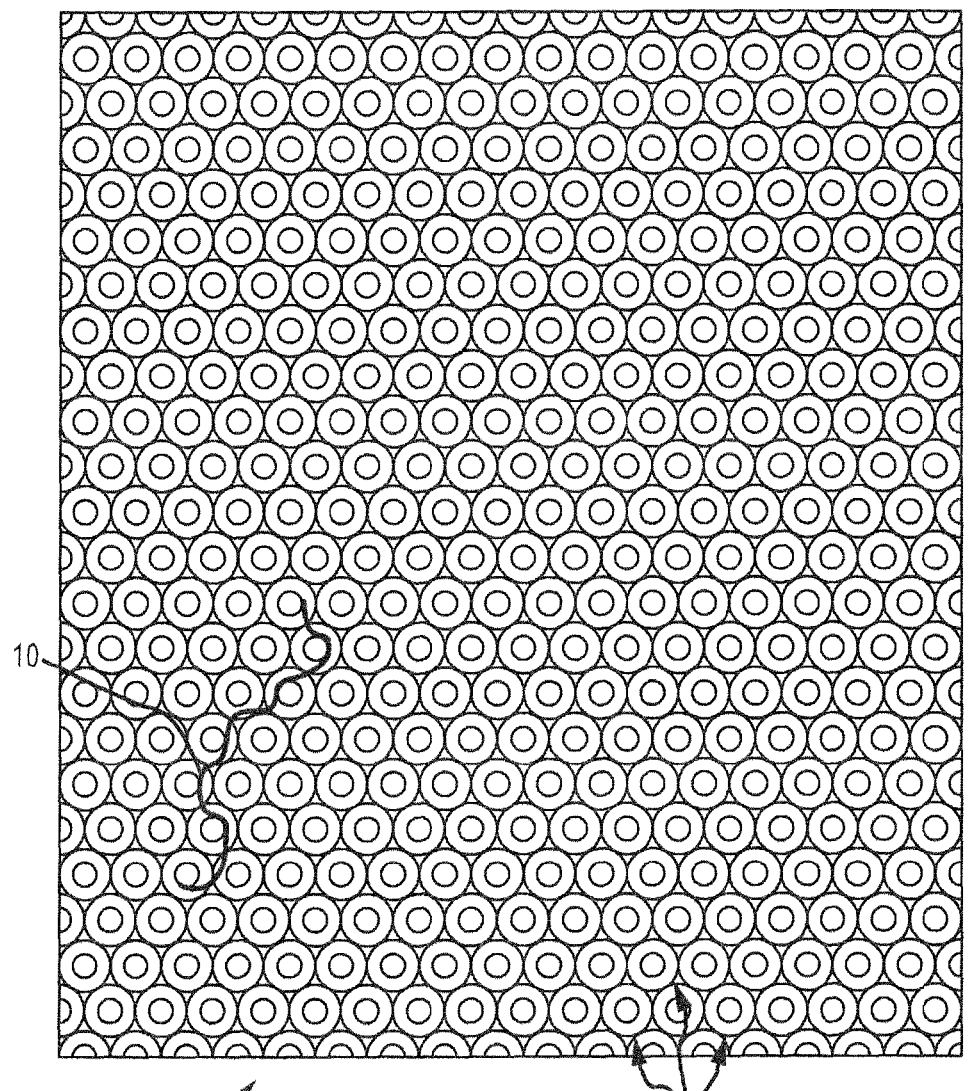
FIGS. 2A and 2B provide top and side views to illustrate a structure for a fluid-circulation layer of the medical pad in an embodiment.
Figure 2B:
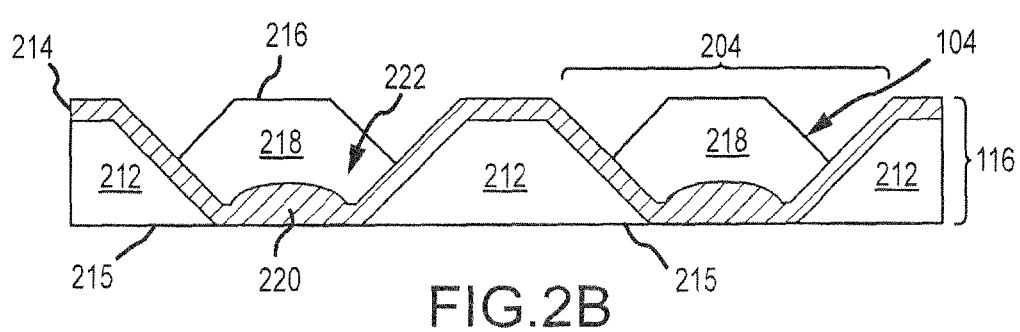

FIGS. 2A and 2B illustrate details of a structure of the circulation layer 116 in an exemplary embodiment with top and side views. The circulation layer 116 comprises a dimple-matrix having a plurality of dimples 204 structured to achieve a desired level of thermal communication with the thermal-exchange fluids in the circulation and containment layers. Fluid paths are provided within the circulation layer 116 by channels 212 formed by the structure of the circulation layer 116 between the dimples 204. This allows the first thermal-exchange fluid to flow in meandering, or tortuous, pathways around the dimples. The availability of multiple meandering paths advantageously allows the first thermal-exchange fluid to flow through the circulation layer 116 with wide coverage, enhancing thermal exchange with the patient's skin and increasing effectiveness of the cooling. An example of a portion of one potential path is illustrated with bold line 210.

The cross-sectional view of FIG. 2B illustrates more particularly how the structure of the dimple matrix defines the channels 212 in one particular embodiment, and how thermal exchange with both the first and second thermal-exchange fluids is achieved. Specifically, a structure 214 (e.g., comprising a polymer-based material) may define the dimple matrix with channels 212 sealably provided between the structure 214 and a sheet-like layer 215 (e.g., comprising a polymer based material). Typically, the structure 214 is formed of a sheet layer of a non-permeable material (e.g., polymer-based material). Formed into the structure 214 are a plurality of depressions 222 and corresponding projections 220 that form the dimples 204. In the present embodiment, the depressions 222 are formed into a top surface of the structure 214 and thereby define corresponding projections 220 on a bottom surface of the structure 214. Accordingly, when the sheet-like layer 215 is disposed over the bottom surface of the structure 214, a top surface of the sheet-like layer 215 is juxtaposed against the projections 220. Thus, the spaces between the projections 220 and the sheet-like layer 215 define the channels 212 and the circulation layer 116. Thermal exchange occurs between the first thermal-exchange fluid and a patient's skin at locations defined by the channels 212 (e.g., spaces between the projections 220 and sheet-like layer 215) where the first thermal-exchange fluid is disposed adjacent to, and thereby in direct or near-direct thermal communication with the skin of the patient when the medical pad is applied.

Thermal exchange between the second thermal-exchange fluid and the patient's skin may occur between the channels 212, at those locations where structure 214 of the circulation layer 116 allows for the second thermal-exchange fluid to fill the depressions 222 of the dimples 204. In the illustrated embodiment, separate enclosed chambers 218 comprising the containment layer 104 may be defined by dimples 204 and overlying obtruded portions 216 to provide adjacent positioning and direct or near-direct thermal communication between the skin of the patient and the second thermal-exchange fluid in the containment layer 104. Like the structure 214, the containment layer 104 is formed is formed of a sheet layer (e.g., upper sheet layer) of a non-permeable material (e.g., polymer-based material) that is molded or otherwise formed to a desired shape and disposed over the upper surface of the structure 214 to define the individual chambers 218 of the containment layer. In various embodiments overlying obtruded portion 216 may be sized to each extend over a plurality of dimples 204 to define separate chambers for containing the second thermal-exchange fluid.

With the illustrated structure, approximately 50% of the skin-contacting side of the circulation layer 116 is provided adjacent to and thereby in direct or near-direct thermal communication with the circulation layer and approximately 50% of the skin-contacting side of the circulation layer 116 is provided adjacent to and thereby in direct or near-direct thermal communication with the containment layer 104. That is, the total area of the bottom surfaces of the depressions 222 may contact 50% of the sheet-like layer 215. Thus, 50% of the sheet-like layer may be in thermal contact with the first thermal-exchange fluid that passes through the circulation layer 116 and 50% of the sheet-like layer 215 may be in thermal contact with the second thermal-exchange fluid contained within the containment layer 104. The structure may be varied in other embodiments to achieve different relative levels of thermal communication between the different layers. For example, in varying embodiments, greater than 20%, greater than 30%, greater than 40%, greater than 50%, greater than 60%, greater than 70%, or greater than 80% of the skin-contacting side of the circulation layer 116 is provided in direct or near-direct thermal communication with the first thermal-exchange fluid. In other embodiments, greater than 20%, greater than 30%, greater than 40%, greater than 50%, greater than 60%, greater than 70%, or greater than 80% of the skin-contacting side of the circulation layer 116 is provided in direct or near-direct thermal communication with the second thermal-exchange fluid.

It is noted that while the embodiment illustrated in FIGS. 2A and 2B generally provides approximately 100% of the skin-contacting side of the circulation layer 116 in communication with one or the other of the thermal-exchange fluids, this is also not a specific requirement of the invention. The total area of the skin-contacting side of the circulation layer 116 may at times have less than 100% of its area in communication with one of the thermal exchange layers. While there may be advantages in treating certain conditions to having 100% of the area in communication with a thermal-exchange fluid purely for treatment reasons, the many varying shapes of parts of the body where treatment may be applied may make it preferable to have configurations in which less than 100% of the area is in thermal communication in order to provide greater structural integrity to the medical pad for such applications, to configure specialized circulation paths for certain areas of the body, or for other reasons such as may be evident to those of skill in the art. In specific embodiments, greater than 50%, greater than 60%, greater than 70%, greater than 80%, or greater than 90% of the area of the skin-contacting side of the circulation layer 116 is provided in thermal communication with one or both of the first and second thermal-exchange fluids.

The level of thermal communication with the different thermal-exchange fluids may also be provided as desired with different configurations of the containment layer. This is illustrated through a comparison of FIG. 3A with FIG. 3B for particular embodiments.

In the drawing of FIG. 3A, the pad is identified generally by reference number 300, with the containment layer 304 having a plurality of chambers 308. The circulation layer 316 is covered on the skin-contacting side with an adhesive layer 320 and removable liner 324.

The drawing illustrates the plurality of chambers 308 extending in a direction along the page, but it will be understood that the chambers 308 may also extend in a direction orthogonal to the page. In a specific embodiment in which the chambers 308 are thus provided in a generally rectangular configuration and each have substantially the same size and shape, the containment layer 304 may thus have a waffle-shaped configuration, but this is not a requirement of the invention. In other embodiments, the sizes of the chambers 308 may differ and the chambers 308 may be organized in other than a rectangular configuration, particularly as might be suitable for application to specific portions of the body or for specialized applications.

In the embodiment of FIG. 3A, fluid in the containment layer 304 is provided in direct thermal communication with the circulation layer 316 so that the dimples 304 of the circulation layer may hold some of the second thermal-exchange fluid. This embodiment also allows the different chambers 304 of the containment layer 304 to be in fluidic communication with each other.

Figure 3B:
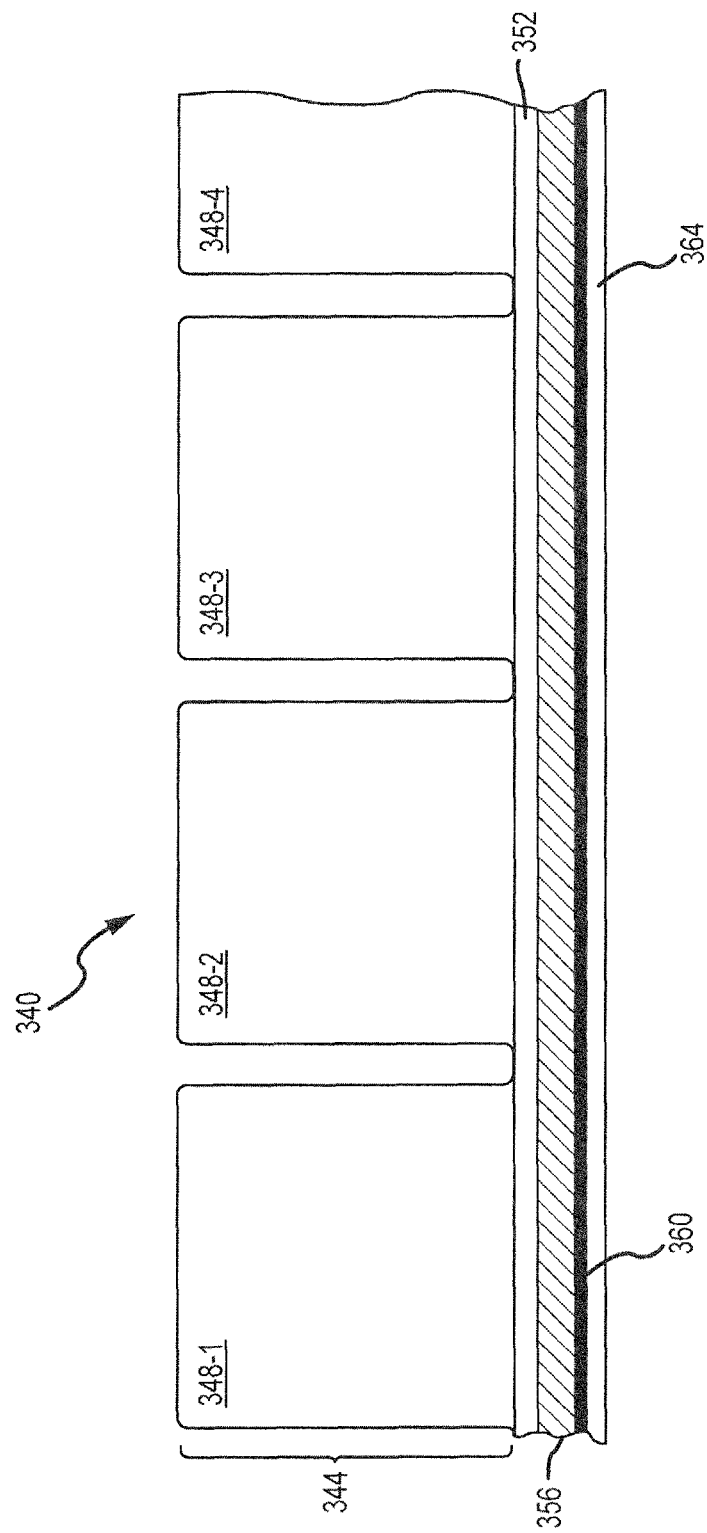

In an alternative embodiment such as illustrated in FIG. 3B, the medical pad 340 includes membrane 352 (e.g., a pliable layer of a polymer-based material) provided between the containment layer 344 and the circulation layer 356, which is also covered by an adhesive 360 on the skin-contacting side and a removable liner 364. The membrane acts to enclose the chambers 348 of the containment layer 344 separately from the circulation layer 356. Such enclosure may be provided in a way that allows fluid communication between the chambers 348 or in a way that prevents fluid communication between the chambers 348, allowing the different chambers individually to encapsulate different thermal-exchange fluids. In some configurations, each chamber 348 might be enclosed individually, although in other arrangements that make use of the membrane 352, the chambers 348 may be enclosed in groups so that fluid communication is provided among separate sets of chambers 348. Such embodiments may be suitable for certain specialized applications in which different thermal properties are desired at different positions of the medical pad.

A number of different thermal-exchange fluids may be used in different embodiments of the invention for both the first and the second thermal-exchange fluids, including gases and liquids such as water. As will be appreciated by those of skill in the art, the thermal-exchange characteristics of the pad 100 may depend on the thermal properties of the thermal-exchange fluids that are used. In particular, some embodiments make use of thermal-exchange fluids that include impurities, which may be in solid, liquid, or gaseous form, to tailor the thermal-exchange properties of the pad.

Table I indicates the thermal properties and densities of certain exemplary materials that may be used in different embodiments and of the thermal properties and densities of biological tissues that may interact thermally with the pad 100.

TABLE I

| Material | Heat Capacity (kJ/kg ° C.) | Thermal conductivity (W/mK) | Density (g/cm$^3$) |
| --- | --- | --- | --- |
| Aluminum | 0.9 | 230 | 2.71 |
| Graphite | 0.7 | 170-370 | 2.2 |
| Copper | 0.38 | 390 | 8.97 |
| Water | 4.186 | 0.57 | 1 |
| Ice | 2.1 | 1.7 | |
| Muscle tissue | 3.6 | 0.36-0.5 | 1 |
| Bone | 1.2 | 0.5 | 2 |
| Fat | 1.67 | 0.186-0.3 | 0.93 |
| Blood | 4 | 0.472-0.62 | 1 |

As noted in the table, a combination of water and a metal or other material such as those listed in the table may yield a greater thermal conductivity. If water is supplemented, for example, with 10 vol. % aluminum or graphite, its thermal conductivity increases by a factor of about 20. By mixing the substances in this way, the fluidic properties of water may advantageously be used while simultaneously increasing thermal conductivity. Although aluminum and graphite have similar thermal-conductivity, the specific-heat capacity of graphite offers additional advantages over the use of aluminum in some embodiments.

In one embodiment, a first thermal-exchange fluid may comprise a liquid such as water for circulation through the circulation layer 116. Further, the second thermal-exchange fluid may comprise liquid of a gel material. In one approach, a cellulose gel material may be utilized that is flowable into the containment layer 104 and curable to assume a shape-holding state within the containment layer 104. For example, a carboxymethyl cellulose (CMC) gel may be utilized that includes aluminum acetate to crosslink the CMC and form a shape-holding gel.

Figure 4:
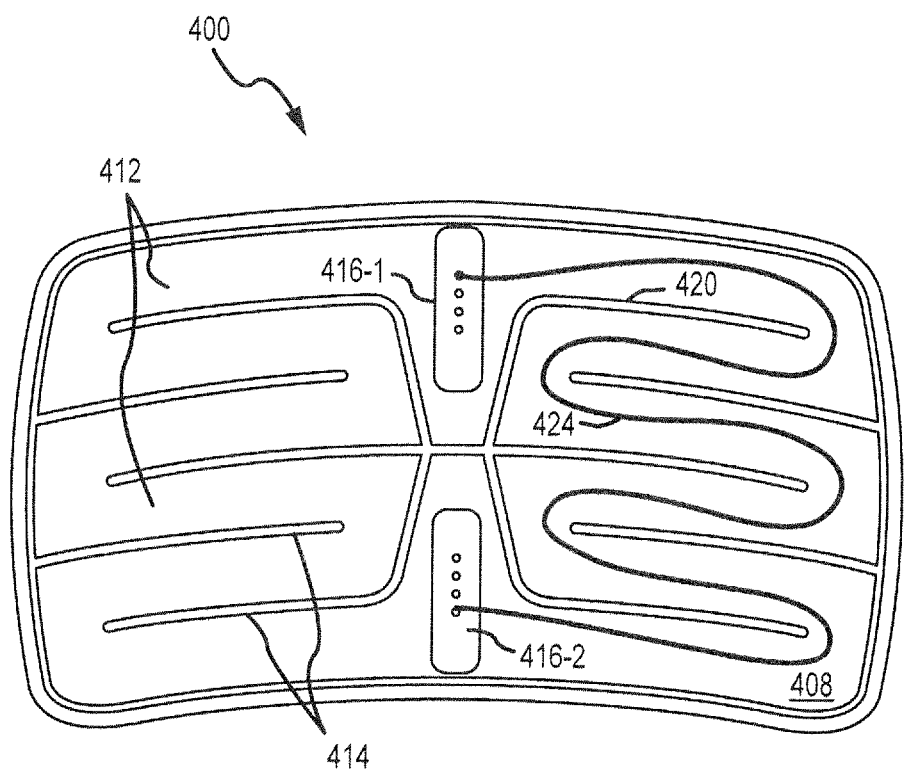
FIG. 4 illustrates an exemplary medical-pad structure for application to a patient in an illustrative embodiment.

FIG. 4 provides one illustration of a medical pad configuration 400 of a circulation layer, as described above, with the patient-facing layer thereof removed. As will be appreciated by those of skill in the art, there are many configurations that may be used depending on such factors as the part or parts of the body to which the medical pad is to be applied, the nature of the condition to be treated, the environment where the condition is to be treated, i.e., whether it is in a hospital, physician's office, accident site, or otherwise.

The configuration 400 includes areas 408 where dimples of the circulation layer (not shown) may be provided, e.g., as described above. Channels 412 may be defined by ribs 414, or raised portions. Fluid is circulated through the circulation layer through fluid ports that may be provided at manifold bonding sites 416 to provide access to the channels 412 within the circulation layer. The location, configuration, and orientation of the ports may be selectively established to provide various advantages. In particular, the ports may be provided to avoid patient weight from creating localized high-pressure areas on the skin by pressing the port or attached tubing against the skin of the patient. Reducing such high-pressure areas reduces the risk of causing pressure ulcers. Also, the tubing can exit off an a patient support platform (e.g., an emergency liter) without multiple turns, thereby reducing the risk of interconnected tubing buckling or kinking, which would limit fluid flow.

The ribs 414 prevent the first thermal-exchange fluid from following a path directly between the input and output ports of the circulation layer, e.g., going directly from site 416-1 to site 416-2. Instead, the first thermal-exchange fluid flows along a path such as illustrated with bold line 424. It is noted that this exemplary path is schematic; at a more detailed level, the actual paths followed by the first thermal-exchange fluid are meandering paths as dictated by the dimple structure of the layer and as explained above in connection with FIGS. 2A and 2B.

Specific configurations for the fluid channels may be as described in, for example, U.S. Pat. No. 6,648,905, the entire disclosure of which is incorporated herein by reference for all purposes. For instance, a first plurality of channels within the circulation layer may be of coincidental, serpentine configuration. More particularly, each of the channels comprising the first plurality of channels may be of a generally S-shaped configuration. Such channels may be of a substantially common length, such as in embodiments where each channel has a length within about 15% of an average length as measured along their respective center paths. Similarly, the channels may also have a substantially common average width, such as in embodiments where each channel has a width within about 25% of an average of the average widths of each channel. A second plurality of channels may also be disposed in a coincidental manner and similarly have substantially common lengths and widths as defined. The structure may also include fluid staging chambers at the fluid ports to distribute fluid and normalize fluid flow through the different pluralities of channels.

Figure 5:
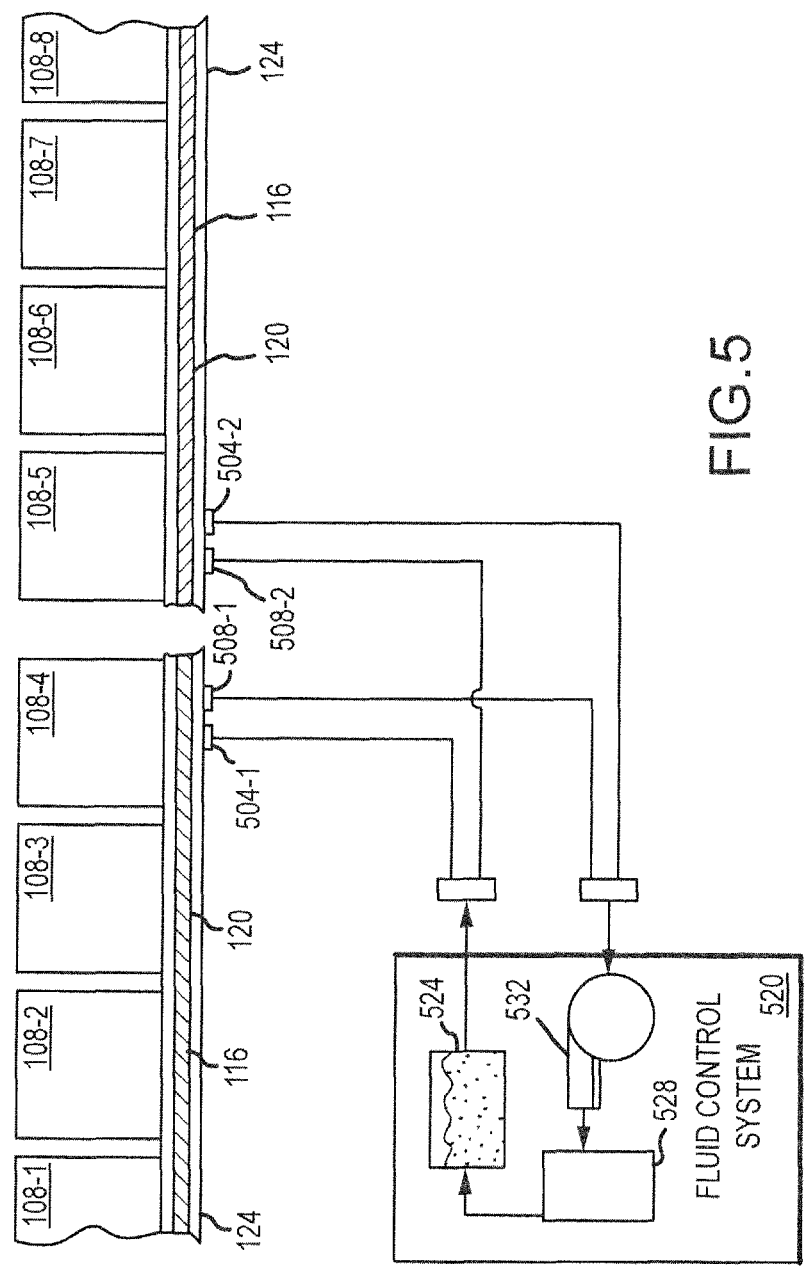
FIG. 5 provides a schematic illustration of a plurality of medical pads fluidly interconnected with a fluid control system.

FIG. 5 provides a schematic illustration of how circulation may be achieved through the circulation layer 116. The drawing shows a plurality of pads, such as may be appropriate for a configuration to be applied to various parts of the body where the shape of the body makes it less effective to use a single pad. For instance, application to the torso may involve the use of a pad 100 for the right side of the patient and a pad 100 for the front side of the body where it curves. Application to the legs might involve separate pads for each of the legs, etc. Each of the plurality of pads 100 is shown to have the same general structure as the pad 100 described in detail in connection with FIG. 1, including both a circulation layer 116 and a containment layer 104 having a plurality of chambers 108.

Fluid may be circulated through the fluid ports 504 and 508 by an interconnectable fluid-control system module 520, such as through interconnected tubing lines. In one arrangement, the fluid-control system module 520 comprises a pump 532 for drawing fluid through the pads 100 under negative pressure, usually less than about −10 psi, although other pressures may be used in different embodiments. At least one thermal-exchange device 528 is provided for cooling the circulated fluid and a fluid reservoir 524.

Figure 6:
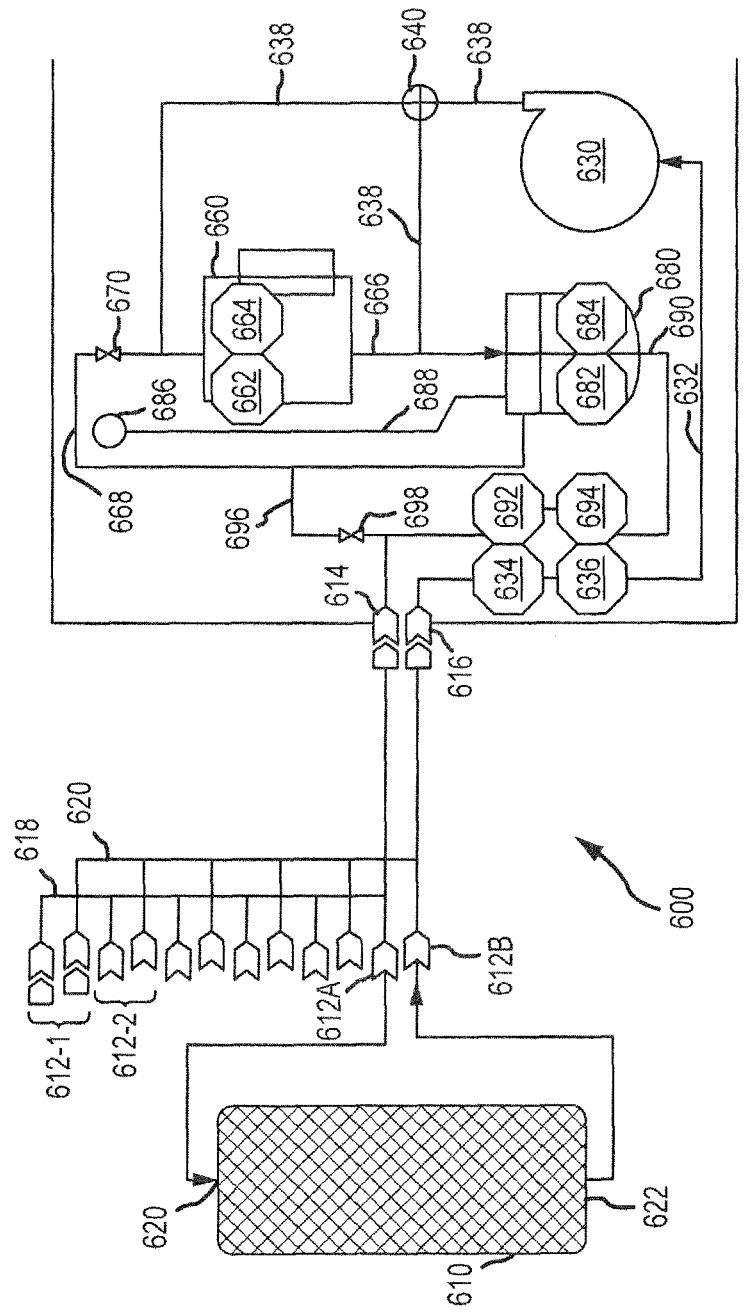
FIG. 6 is a fluid-circuit diagram illustrating on embodiment of a medical pad and related fluid-circulation system in accordance with an embodiment of the invention.

A fluidic circuit diagram is shown in FIG. 6 to illustrate in greater detail how fluid is circulated through the medical pad, designated by reference number 610 in the drawing. The medical pad is connected with the fluid circulating system 600 using pad-connector pairs 612. Each pad-connector pair 612 includes an inlet connector 612A for connection with an inlet 620 of the medical pad 610 and an outlet connector 612B for connection with an outlet 622 of the medical pad 610. Both the inlet and outlet connections may be made with flexible tubing or similar structure suitable for fluidic connection. Merely by way of illustration, the embodiment shown includes six pad-connector pairs 612 to permit connection of six medical pads 610 with the fluid circulating system 600. But it should be appreciated that the invention is not limited by the number of pad-connector pairs 612 and that different embodiments might have a greater or lesser number of pad-connector pairs 612. Each inlet connector 612A of the pad-connector pairs 612 is connected via an inlet feeder line 618 to a main inlet connector 614, and each outlet connector 612B of the pad-connector pairs 612 is connected via an outlet feeder line 620 to a main outlet connector 616. The fluid circulating system 600 also includes a pump 630, a temperature storage module 660, and a fluid reservoir 680.

The pump 630 is connected downstream via a pump inlet line 632 from the main outlet connector 616 and is preferably self-priming. A temperature sensor 634 and a pressure sensor 636 in the pump inlet line 632 measure the temperature and pressure respectively of the fluid exiting the pad 610 or pads connected with the fluid circulating system 600. Information from the pressure sensor 636 may be used in controlling the speed of the pump 630 so that generally constant negative pressure is maintained. The pump 630 is connected upstream via pump outlet lines 638 and a three-way valve 640 with both the reservoir 680 and the temperature storage module 660.

The temperature storage module 660 includes cooling elements 662 and a temperature sensor 664. The cooling elements 662 may be activated to cool fluid within the temperature storage module 660 to a desired temperature detectable by the temperature sensor 664. The temperature storage module 660 is connected via a primary temperature storage module outlet line 666 upstream from the reservoir 680 so that fluid that has been cooled to a desired temperature within the temperature storage module 660 flows therefrom to the reservoir 680 while the pump 630 is operating, i.e., pumping fluid therethrough. The three-way valve 640 may be regulated to control the proportion of fluid that flows to the reservoir 680 directly from the pump 630 and the portion of fluid that flows from the pump 630 through the temperature storage module 660 to the reservoir 680 in order to control the temperature of the fluid flowing into the pad 610. The temperature storage module 660 is also connected via a secondary temperature storage module outlet line 668 to the reservoir 680. A normally open valve 670 in the secondary temperature storage module outlet line 668 permits fluid to drain from the temperature storage module 660 to the reservoir 680 when the pump 630 is not operating.

The fluid reservoir 680 includes a level sensor 682 for detecting a level of fluid within the reservoir 680 and cooling element 684 for precooling fluid within the reservoir 680. When desirable, such as when the level sensor 682 indicates that the fluid level has fallen below a specified level, additional fluid may be added to the reservoir through a fill port 686 that is connected with the reservoir 680 by a fill line 688. Preferably, the reservoir 680 has a nonmixing inlet and outlet in order to minimize undesirable temperature variations of fluid within the reservoir. The outlet of the reservoir 680 is connected via a reservoir outlet line 690 to the main inlet connector 614. A temperature sensor 692 and a flow sensor 694 may be provided in the reservoir outline 690. The temperature sensor 692 measures the temperature of fluid provided to the pad inlets via the inlet feeder line 618. Information from the temperature sensor 692 may be used in regulating the three-way valve 640 to control the fluid temperature. Information from the flow sensor 694 and the temperature sensor 634 in the pump inlet line 632 may be used in determining the heat transfer between the patient and pads connected to the fluid circulating system 600. A drain line 696 with a normally closed two-way valve 698 is provided for draining the pads to the reservoir 680 when the cooling procedure is complete.

Other configurations may be used for the fluid circulating system 600 in alternative embodiments, examples of which are illustrated and described in commonly assigned U.S. Pat. No. 6,197,045, the entire disclosure of which is incorporated herein by reference for all purposes.

Figure 7:
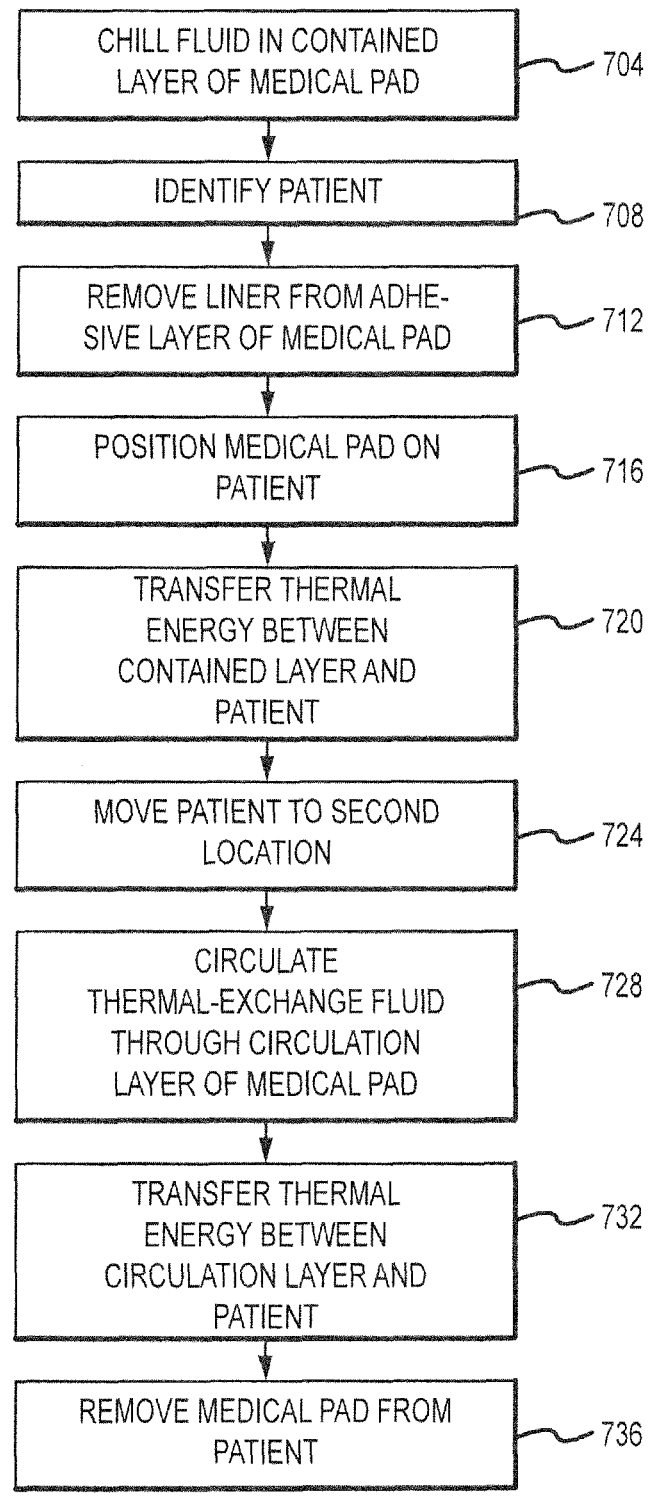
FIG. 7 is a flow diagram summarizing methods of using a medical pad in accordance with embodiments of the invention.

FIG. 7 provides a flow diagram that illustrates methods for using a medical pad in accordance with embodiments of the invention. While the flow diagram sets for specific functions that are performed and illustrates them in an exemplary order, these are not intended to be limiting. In various alternative embodiments, some of the functions may be omitted, others not specifically illustrated may additionally be performed, and/or the order may be changed from that illustrated specifically in the drawing.

The method begins at block 704 by chilling the second thermal-exchange fluid in the containment layer of the medical pad. As previously noted, different thermal-exchange fluids may be used in different embodiments and therefore the phase-transition points of the fluid may differ in different embodiments. In some embodiments, the second thermal-exchange fluid has a freezing point equal to or less than 0° C. In those embodiments where the second thermal-exchange fluid comprises water mixed with another substance, the freezing point may be higher or lower than 0° C. In certain embodiments, the second thermal-exchange fluid may comprise a liquid such as water comprising a shape-holding gel material that may be chilled to 0° C. or less, such that the liquid is in a frozen state or at least a partially frozen state at block 704, and wherein the shape-holding gel maintains an initial configuration as the second thermal-exchange fluid warms during use.

It is also noted that chilling the second thermal-exchange fluid at block 704 may or may not involve a phase change in the fluid. For example, if the second thermal-exchange fluid is pure water, it may be chilled to a temperature on either side of its freezing point of 0° C. without deviating from the intended scope of the invention. Indeed, even if the second thermal-exchange fluid is frozen as part of the chilling at block 704, it is still considered to be a "fluid" as the term is used herein. Further, if the second thermal-exchange fluid has an evaporation point that is crossed as part of the chilling at block 704 so that it changes phase from a gas to a liquid, it is still considered to be a "fluid" as the term is used herein.

Use of the medical pad is generally expected to result in the transfer of thermal energy to the second thermal-exchange fluid, and such transfer may result in reversal of a phase change that occurs as part of the chilling at block 704. Such embodiments are also specifically intended to be within the scope of the invention.

At block 708, a patient is identified who is expected to benefit from application of a cooling therapy. The patient may be suffering from a stroke, head trauma, or other injury or disease that may be effectively treated with cooling therapy. It is specifically noted, though, that it is not a requirement of the invention that the patient be suffering from any type of disorder, whether it be an injury-caused disorder or otherwise. In some embodiments, the cooling therapy may be used as an adjunct to the application of other medical procedures, such as where a patient undergoing surgery is identified as likely to benefit from the application of cooling therapy.

The medical pad is applied to the identified patient at blocks 712 by removing a liner or plurality of liners from the adhesive layer, depending on whether the embodiments use a generally continuous adhesive layer or have a plurality of adhesive strips. In embodiments where no adhesive is used, block 712 may be omitted. At block 716, the medical pad is positioned on the patient. It is generally expected that the pad will be placed in contact with skin tissue with the adhesive being used to adhere the pad to the skin and thereby generally maintain its position on the patient during the cooling therapy. But in alternative embodiments, the pad may be positioned on other types of tissue, although such embodiments may omit the use of an adhesive.

The nature of the medical pad as described above, particularly its thermal properties, allows a transfer of thermal energy between the contained layer and the patient at block 720. The transfer results in cooling of the patient, at least locally in the area where the pad is applied and with consequent heating of the second thermal-exchange fluid.

At block 724, the patient is moved to a second location where the first thermal-exchange fluid may be circulated through the circulation layer of the medical pad at block 728. This results in thermal energy being transferred between the circulation layer and the patient at block 732. To realize fluid circulation, the medical pad may be selectively interconnected to a fluid control system. Circulation of the first thermal-exchange fluid may be achieved using the fluid control system as described in connection with FIGS. 5 and 6 and as also described in commonly assigned U.S. Pat. Nos. 6,197,045, 6,648,905, and 6,799,063, all of which are incorporated herein by reference in their entireties.

Movement of the patient at block 724 may take place in a number of different ways that reflect a variety of implementations of the invention. Such movement also combines with other aspects of the invention, particularly including the use of two thermal-exchange fluids that are used differently, to achieve numerous benefits. For example, there may be circumstances in which an appropriate fluid-control system is not available at the location where the medical pad is applied to the patient at block 716. This may occur, for instance, in emergency settings where a medical pad of the type described herein is maintained in an ambulatory vehicle for access by paramedics who do not have access to the fluid-control system at the emergency site. It may also occur in settings where a physician maintains medical pads of the type described herein at his or her office, but where the fluid-control system is maintained at a hospital. Still other settings where such circumstances may exist include clinics or nurses' offices in schools, which might maintain medical pads for use, but which lack the larger and more specialized fluid-control system equipment.

Irrespective of the particular circumstances, the combination of a containment layer and a circulation layer in a single medical pad provides a number of benefits in the treatment of conditions where cooling therapy is of value. While medical pads that include a circulation layer can provide effective cooling, the lack of ready availability of a fluid-control system at the site where the patient is first encountered risks losing time that may be critically important in preventing biological damage that could be mitigated with cooling therapy. Mere application of a cool substance such as ice is less effective for many reasons. As noted above, the second thermal-exchange fluid may be a substance that is better adapted for thermal exchange by having thermal-exchange properties that are more effective. Medical pads that include an adhesive also aid in maintaining a constant position on the patient for application of the cooling therapy. In addition, the integrated medical pad is already prepared in position on the patient for use with a fluid-control system when a location has been reached where such usage is possible. Timing for application of the cooling therapy can be critical in achieving the benefits of the therapy and the combination described herein can decisively make a difference in the level of irreversible biological damage that occurs to the patient, even preventing irreversible damage entirely in some cases.

Once the treatment has been applied, the medical pad may be removed from the patient at block 736. In conjunction with such removal, the medical pad may be disconnected from the fluid control system and disposed of.

Figure 8:
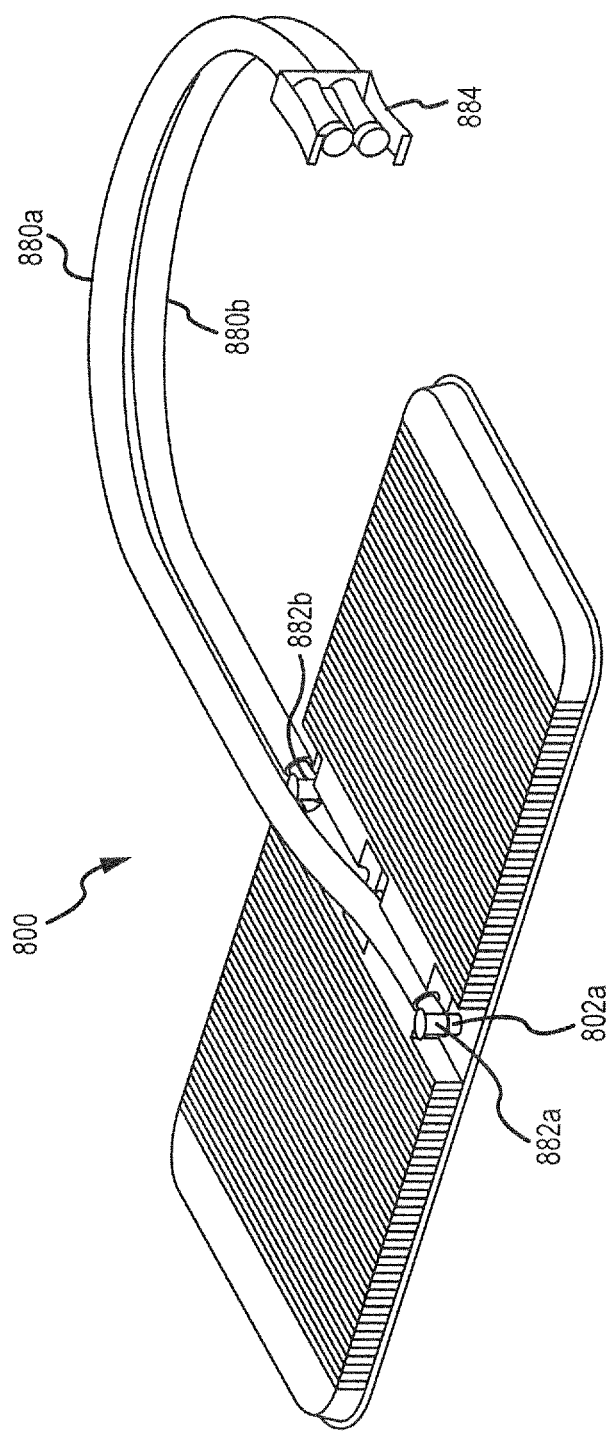
FIG. 8 illustrates another configuration of a medical pad embodiment.

FIGS. 8-13A and 13B illustrate another embodiment of a medical pad 800. As shown in FIGS. 8 and 9, fluid circulation lines 880a, 880b may be provided to circulate a first fluid thermal-exchange through the medical pad 800. For example, a connector 882a provided at a first end of fluid circulation line 880a may be fluidly interconnectable to a fluid inlet port 802a of medical pad 800, and a connector 882b provided at a first end of fluid circulation line 880b may be fluidly interconnectable to a fluid outlet port 802b of medical pad 800. Second ends of fluid circulation lines 880a, 880b may be provided for selective interconnection to and disconnection from a fluid control system of a type referenced hereinabove. In the illustrated embodiment, a connector device 884 may be provided at the second ends of the first and second fluid circulation lines 880a, 880b for interconnection with the fluid control system. In one approach, connector device 884 may be of a type described in U.S. Pat. No. 6,827,728.

Figure 9A:
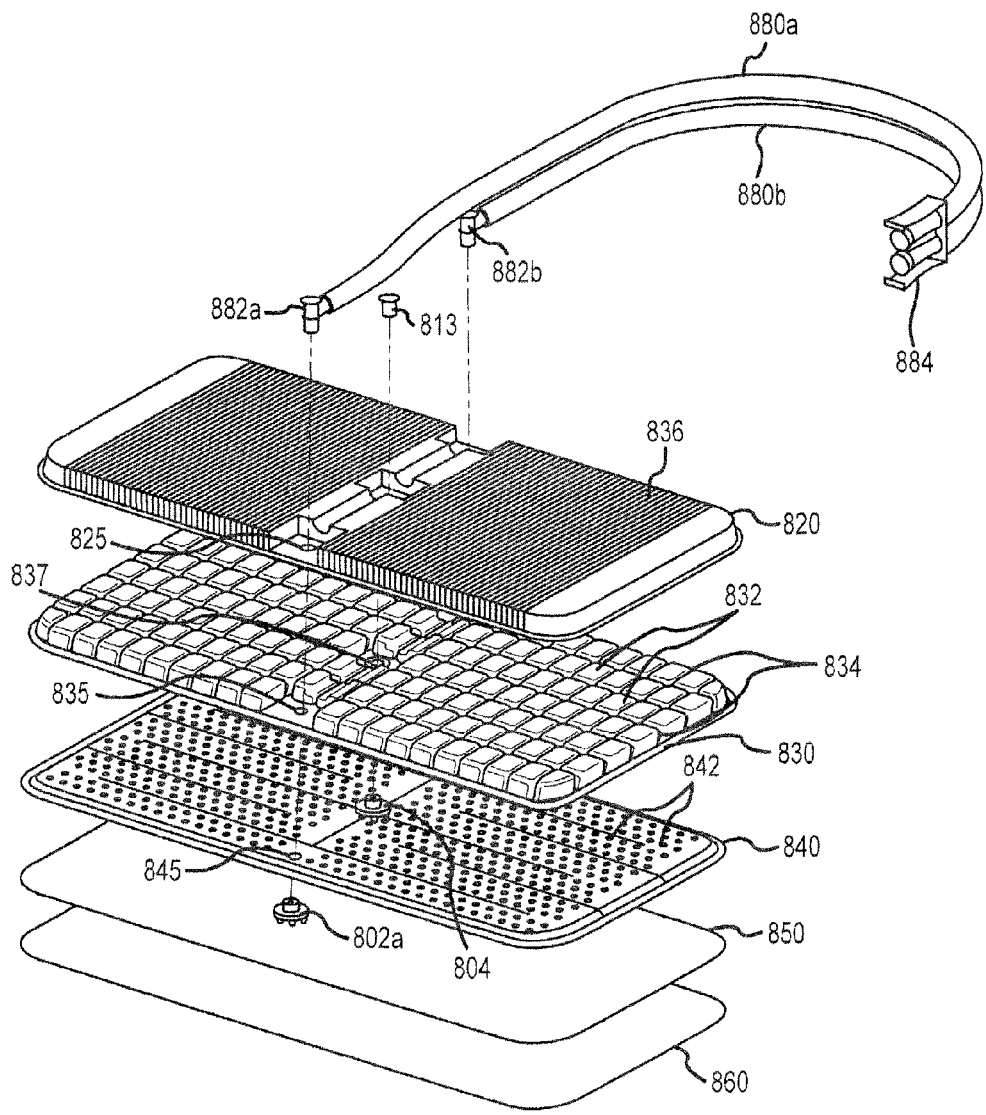
FIG. 9A is an exploded assembly view of the medical pad embodiment of FIG. 8.
Figure 9B:
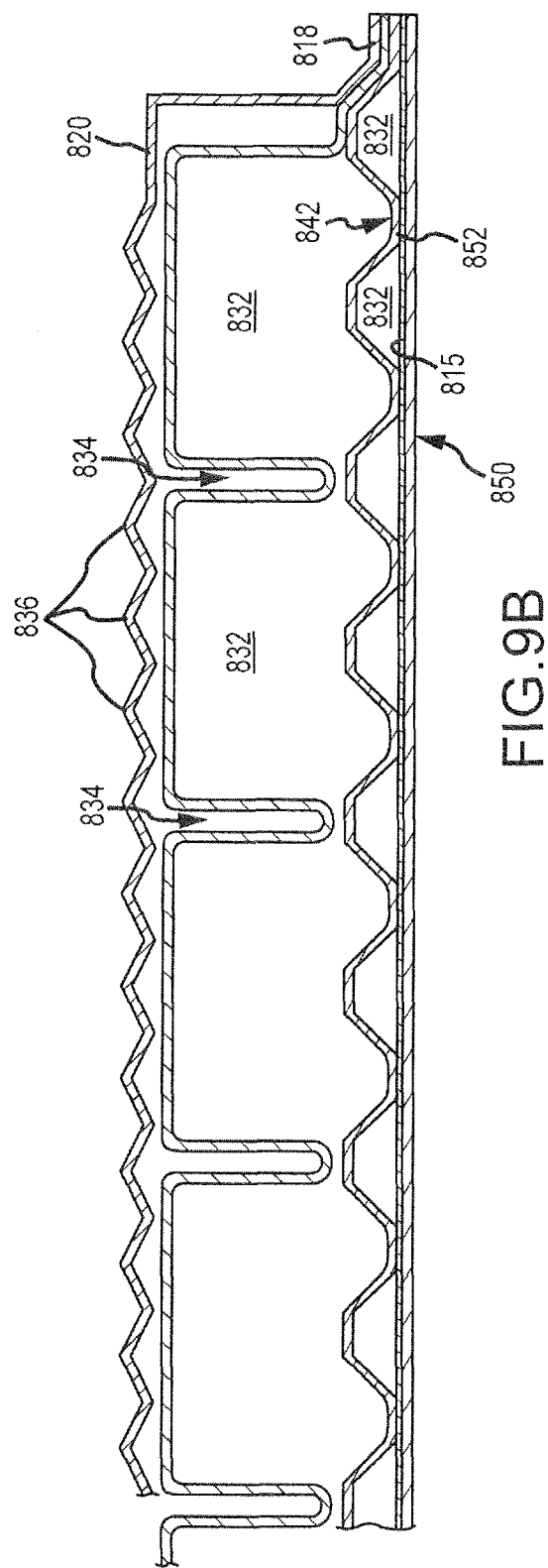
FIG. 9B is a cross-sectional view of the medical pad embodiment of FIG. 8.
Figure 9C:
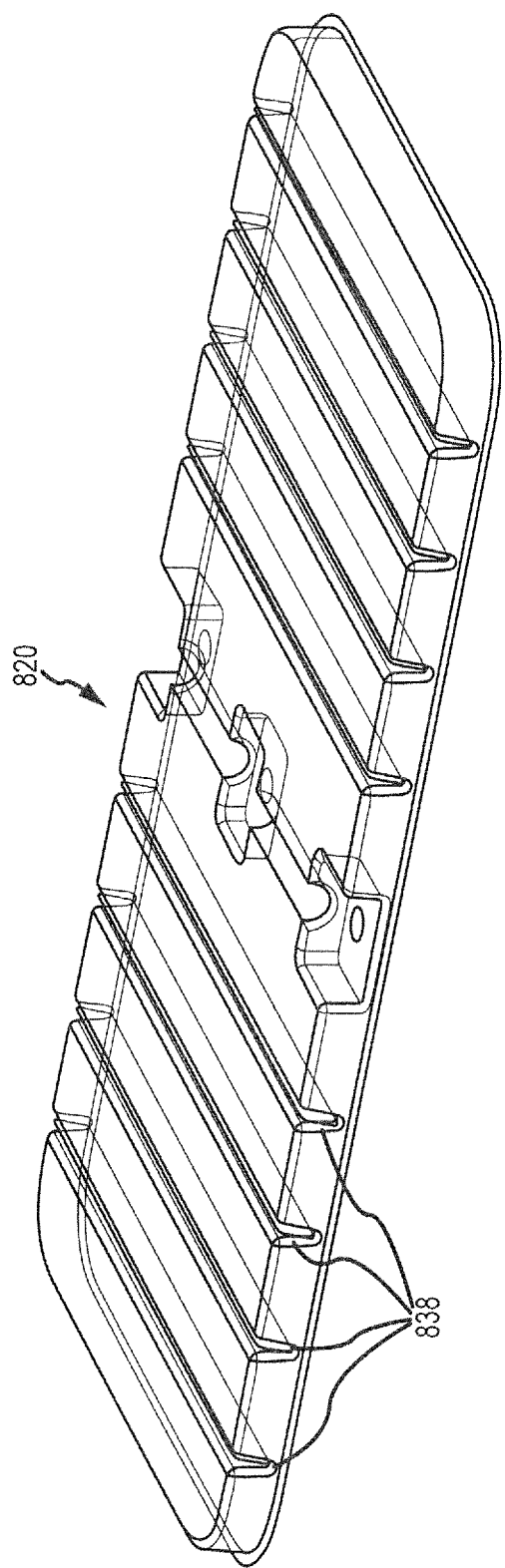
FIG. 9C is a perspective view of an alternate top layer that may be utilized with the medical pad of FIGS. 8 and 9A.

Reference is now made to FIGS. 9A and 9B which further illustrates medical pad 800. In the illustrated embodiment, medical pad 800 may include a top layer 820, a containment layer 830, an intermediate layer 840, an interface layer 850, and a bottom layer 860. As illustrated, the various layers may be arranged in a stacked, or laminate, fashion, and may be of a substantially common configuration (e.g., rectangular). In the later regard, various additional configurations are envisioned, including configurations designed for specific anatomic regions of use.

The intermediate layer 840 and interface layer 850 may be provided to define a circulation layer (e.g., channels 852; see FIG. 9B) therebetween, wherein a first thermal-exchange fluid may flow into and out of such circulation layer via fluid circulation lines 880a, 880b. Further, the intermediate layer 840 and containment layer 830 may be provided to define a containment layer therebetween for containing a second thermal-exchange fluid disposed in, for example, one or more chambers 832. FIG. 9B, also illustrates a sheet-like layer 815 having a top surface disposed adjacent to the bottom surface of the intermediate layer 840 as previously discussed in relation to FIG. 2B. As shown, a top surface of patient interface layer 850 is juxtaposed against the bottom surface of sheet-like layer 815.

As will be appreciated, a second thermal-exchange fluid contained in the containment layer may be provided to cool a patient, independent from and/or in overlapping relation with the circulation of a first thermal-exchange fluid through the fluid circulation layer. Further, a first thermal-exchange fluid may be circulated through the fluid circulation layer to cool a patient, independent from and/or in overlapping relation with the patient cooling by a second thermal-exchange fluid contained within the containment layer.

In one approach, adjacent ones of the top layer 820, containment layer 830 and intermediate layer 840 may be interconnected about the peripheries 818 thereof (e.g., via RF welding of copolymer materials comprising such layers). See FIG. 9B. The interface layer 850 may be connected across a top side thereof to a bottom side of intermediate layer 840. The interface layer 850 may define an adhesive surface or layer. In one approach, the patient interface layer 850 may comprise a hydrogel material disposed across the lateral extent of the bottom side of the intermediate layer 840 (e.g., across all or substantially all of the bottom side of the medical pad). For example, hydrogel materials may be utilized that comprise a polymer/water matrix marketed by AquaMed Technologies of Langhorne, Pa., U.S.A. The patient interface layer 850 may further include a removable liner that may be readily removed from the adhesive surface of the interface layer 850 at the time of placement of medical pad 800 on a given patient for contact cooling (e.g., direct adhesive engagement with the skin of a patient). The adhesive surface may display a peel value at initial skin application of about 20 g/in. to 80 g/in. to facilitate fixed positioning on a patient, yet facilitate removal after use.

As illustrated in FIGS. 9A and 9B, the containment layer 830 may comprise a plurality of chambers 832 that project upward and away from a bottom side of the containment layer and upward from a top side of the intermediate layer, with indentations 834 between such chambers 832. A top side of the intermediate layer 840 may be provided with a plurality of depressions 842, e.g., a dimple-matrix, extending across the lateral extent thereof. Correspondingly, a bottom side of the intermediate layer may be provided with a plurality of projections 854. Collectively, the spaces between the projections 854 on the bottom surface of the intermediate layer 840 and the top surface of the interface layer 850 define fluid flow channels 852 of the circulation layer. In one approach, the chambers 832 and depressions 842 may be disposed in opposed, face-to-face relation for fluid communication therebetween. In this regard, at least a portion of a second thermal-exchange fluid contained by the containment layer may be contained by the plurality of depressions 842 and the plurality of chambers 832 defining the containment layer.

In one approach, the chambers 832 and indentations 834 may be arranged in rows and columns to facilitate flexure of the medical pad along the indentations 834 for conformal engagement of medical pad 800 with a patient. In this regard, each of the layers 820, 830, 840 and 850 may be of a pliable construction to facilitate curvature, or flexure, along the lateral and/or longitudinal dimensions thereof. By way of example, each of the layers may comprise a copolymer material such as a polyolefin material (e.g., ethylene-vinyl acetate).

Top layer 820 may be provided to define an insulative layer, or air space, between the top layer 820 and containment layer 830. In this regard, such insulative layer may surround chambers 832 to enhance thermal exchange between the second thermal-exchange fluid and a patient during use. That is, the insulative top layer 820 provides a pocket of trapped air that acts to insulate the upper surface of the chambers 832 in the containment layer 830. Further, to enhance flexibility of the top layer 820, a series of corrugations 836 may extend across the width of the top layer 820. Such corrugations 836 allow the top layer to stretch and compress to facilitate flexure of the underlying chambers 832 when the medical pad 800 is applied to a non-planar surface.

Figure 9D:
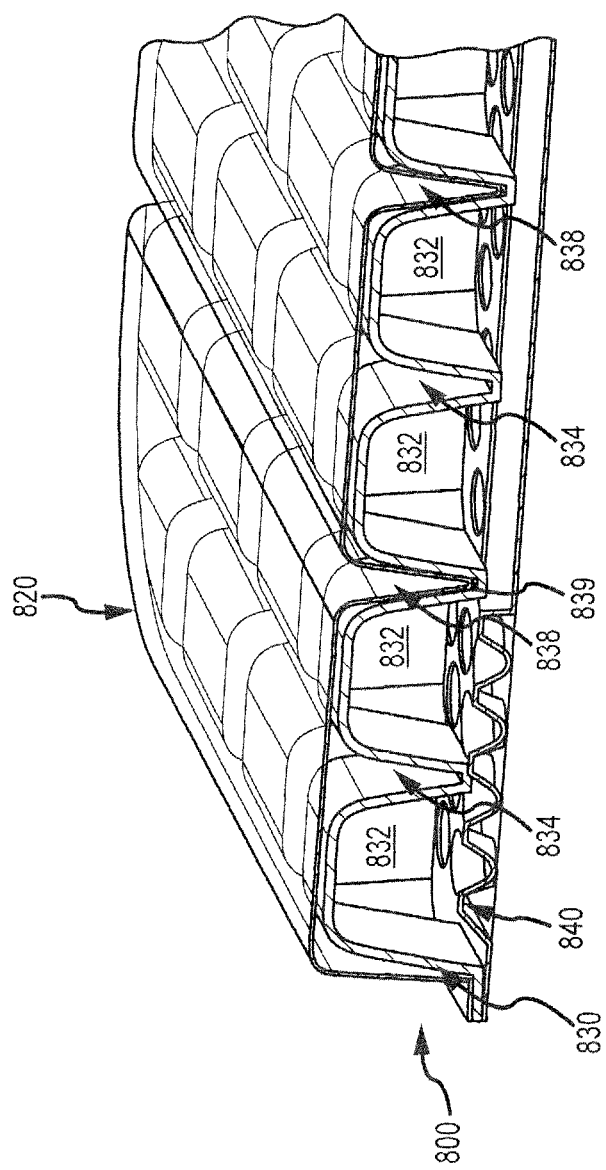
FIG. 9D is a partial cross-sectional view of a medical pad incorporating the top layer of FIG. 9C.

In another embodiment illustrated in FIGS. 9A and 9D, the top layer 820 includes a plurality of indentations or recesses 838 that extend across a lateral extent thereof. As shown, these recesses are significantly deeper as measured from a top surface of the top layer 820 as compared to the corrugations 836 as illustrated in FIG. 9A. Accordingly, these recesses 838 permit greater flexibility of the top layer 820 and, hence, the underlying layers of the medical pad 800. In order to provide recesses 838 having such an increased depth, it is in some instances necessary that the top layer recesses be positioned between indentations 834 between the chambers 832 of the underlying fluid containment layer 830. This is illustrated in the partial cross-sectional view of FIG. 9D. As shown, the bottom 839 of the top layer recesses extend into the indentations 834 between adjacent rows of chambers 832 of the fluid containment layer. Stated otherwise, the top layer recesses 838 extend below a top surface of the fluid containment layer as defined by the top surfaces of the individual chambers 832.

In the illustrated embodiment, the top layer recesses 838 extend across a lateral width of the top layer in an accordion-shaped configuration. These recesses allow the top layer to expand and collapse. However, it will be appreciated that the top layer may incorporate recesses in other configurations such as across its lateral length in instead of and/or in addition to the recesses across its lateral width. That is, the top layer recesses 838 may define a waffle-shaped configuration similar to the indentations 834 between the chambers 832 in the fluid containment layer. Such an arrangement may allow the top layer to expand and/or collapse in two or more directions. Further, the number and/or spacing of top layer recesses 838 may be varied. For instance, while the top layer recesses 838 are disposed in the indentations 834 between every other row of chambers 832 in the fluid containment layer as shown in FIG. 9D, such top layer recesses may be disposed between every row of chambers, every third row, etc. Likewise, if top layer recesses are provided between the columns of chambers 832, the number and/or spacing of such indentations may also be varied. Further, the number and/or spacing of the recesses may be varied independently across the lateral width and lateral length of the medical pad. For instance and by way of example only, the recesses may be disposed between every other set of adjacent chamber rows and between every third set of adjacent chamber columns.

To provide desired flexibility, the depth of the top layer recesses 838, as measured from the top surface of the top layer to their bottom surfaces 839, may also be varied. In one embodiment, the top layer recesses 838 have a depth extends into at least 20% of the depth of the fluid containment layer indentations 834, as measured from the top of the chambers 832 to the bottom of the fluid containment layer indentations 834. Further, in varying embodiments, the top layer recesses 838 may extend over greater than 30%, greater than 40%, greater than 50%, greater than 60%, greater than 70%, or greater than 80% of the depth of the fluid containment layer indentations 834.

To further facilitate conformal positioning of medical pad 800 and/or enhanced thermal transfer between a patient and a first thermal-exchange fluid circulated through the circulation layer, the depressions 842 may be arranged in staggered rows and columns. In this regard, the depressions 842 on the top side of intermediate layer 840 provide corresponding projections on the bottom side of intermediate layer 840. In turn, tortuous flow paths around the projections may be defined within the fluid circulation layer.

Figure 9E:
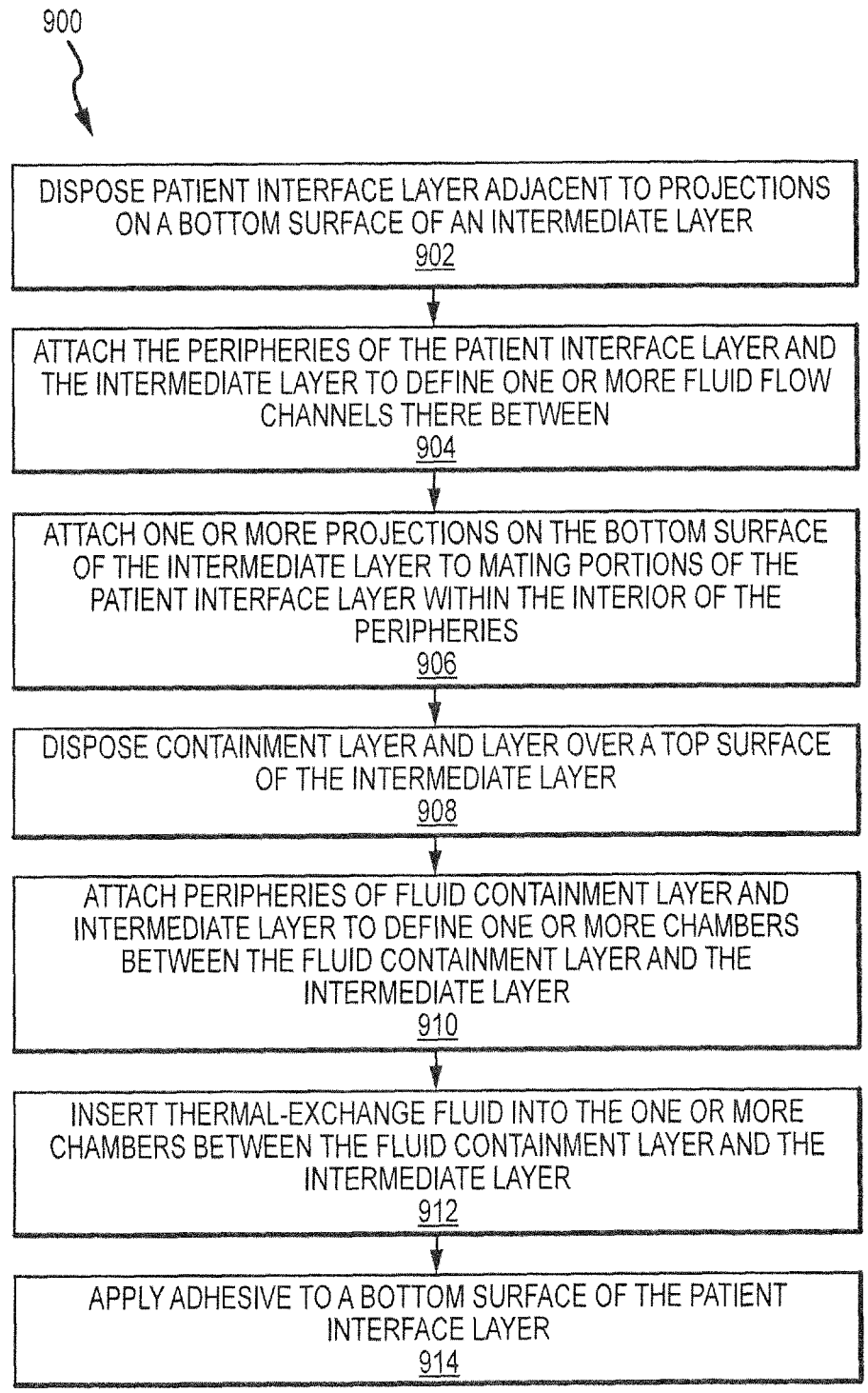
FIG. 9E is a flow diagram summarizing a first process for forming the medical pad of FIG. 8.

FIG. 9E illustrates a process (900) for forming the medical pad such as the medical pad illustrated in FIG. 9A. The process (900) includes disposing (902) a top surface of a patient interface layer 850 below the bottom surface of an intermediate layer 840 such that a plurality of flow channels are defined between projections 854 on the bottom surface of the intermediate sheet layer 840 and the top surface of the patient interface layer 850. Once properly aligned, peripheries of the patient interface layer 850 and the intermediate layer 840 are attached (904) to form a fluid tight connection there between. Such attachment may be performed in any appropriate manner including use of adhesives. In one preferred embodiment, the peripheries of these layers 840, 850 are welded via RF welding. In such an embodiment, the patient interface layer 850 and intermediate layer 840 may be placed in dies that are configured to compress the peripheries of the layers 850 and 840 together and provide RF energy between mating portions of the dies about these peripheries. In a further optional step, one or more mating interior locations of the intermediate layer 840 and patient interface layer 850 (e.g., within the peripheries of these layers) may likewise be attached (906). For instance, some or all of the projections 854 on the bottom surface of the intermediate layer may be attached to adjacent portions of the patient interface layer. Alternatively, ribs formed on the bottom surface of the intermediate layer 840 may be attached to adjacent portions of the patient interface layer (e.g., FIG. 4) free of attachment of the projections on the bottom surface of the intermediate layer to the patient interface layer. Stated otherwise, less than all of the projections (e.g., ribs and/or dimple projections) on the bottom surface of the intermediate layer 840 may be attached to the patient interface layer 850. Again, such attachment of the projections within the peripheries of the intermediate layer 840 and patient interface layer 850 may utilize specially configured dies to compress mating portions together and thereafter apply RF energy to affect RF welding. It will be appreciated that the attachment of the peripheries and mating interior locations may be performed in a common process.

Once the intermediate layer 840 and patient interface layer 850 are attached, a containment layer 830 and/or the containment layer 830 and a top insulating layer 820 may be disposed (908) over a top surface of the intermediate layer 840. Once properly aligned, the peripheries of the containment layer 830, intermediate layer 840 and, if provided, top insulative layer 820 may be attached (910) about their peripheries. Such attachment may form a fluid tight connection between the peripheries of these layers 830, 840 and/or 820. The attachment between the intermediate layer 840 and the fluid containment layer 830 defines a fluid tight compartment having one or more chambers 832 adapted to hold a second thermal-exchange fluid.

After attaching the fluid containment layer 830 and the intermediate layer 840, the second thermal-exchange fluid is introduced (912) into the chamber(s) 832 defined between the intermediate layer 840 and the fluid containment layer 830. Such fluid introduction may include pumping fluid between first and second ports or vacuum filling as discussed here and in relation to FIGS. 14A and 14B. In any case, once the second thermal-exchange fluid is introduced into the chambers, and adhesive surface may be applied (914) across a lateral extent of the bottom side of the patient interface layer 850.

Figure 9F:
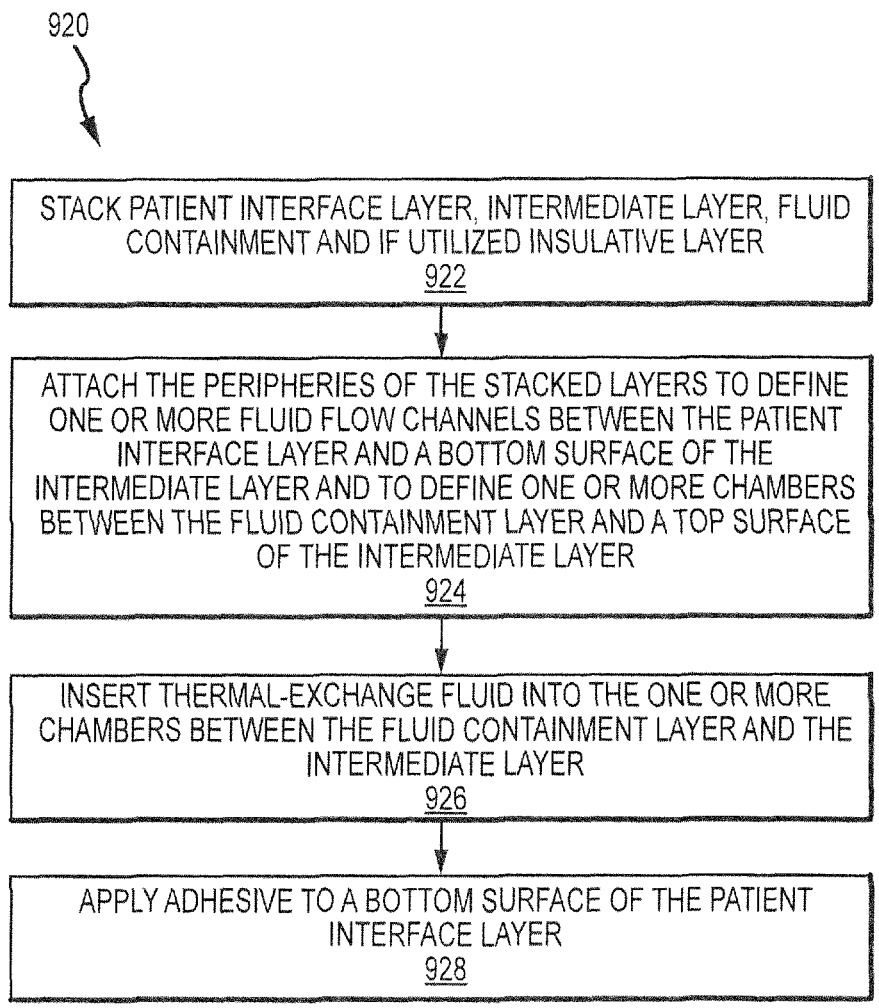
FIG. 9F is a flow diagram summarizing a second process for forming the medical pad of FIG. 8.

FIG. 9F illustrates a second process (920) for forming the medical pad such as the medical pad illustrated in FIG. 9A. In this process (920), multiple layers 850, 840, 830 and if utilized 820 are stacked (922). More specifically, a top surface of a patient interface layer 850 is disposed below a bottom surface of an intermediate layer 840 such that a plurality of flow channels are defined between projections on the bottom surface of the intermediate sheet layer 840 and the top surface of the patient interface layer 850. Specifically, a plurality of flow channels are defined between projections on the bottom surface of the intermediate layer 840 and the top surface of the patient interface layer 850. A bottom surface of a fluid containment layer 830 is disposed over a top surface of the intermediate layer 840. If utilized, a top insulative layer is disposed over a top surface of the fluid containment layer 830. Once properly oriented, peripheries of the multiple layers 850, 840, 830 and if utilized 820 are attached (924) to form fluid tight connections therebetween. Again, such attachment may utilize adhesives or welding such as RF welding. A second thermal-exchange fluid is then introduced (926) into one or more chamber(s) 832 defined between the intermediate layer 840 and the fluid containment layer 830. Such fluid introduction may include pumping fluid between first and second ports or vacuum filling as discussed here and in relation to FIGS. 14A and 14B. Once the second thermal-exchange fluid is introduced into the chambers, and adhesive surface may be applied (928) across a lateral extent of the bottom side of the patient interface layer 850.

Sealing the peripheries of the different layers allows for disposing the patient interface layer 850 against the projections 854 on the bottom surface of the intermediate layer 840, and/or sheet-like layer 815 if utilized, free of direct mechanical connection of some or all of the projections and mating portions of the sheet-like patient interface layer. That is, the patient interface layer 850 may be juxtaposed against the projections without mechanical connection therebetween. As fluid flow through the fluid circulation layer is under negative pressure, the lack of physical connection does not result in bulging of the sheet-like layer away from the projections. Rather, the patient interface layer 850 is drawn against the projections. Such an arrangement has been found useful for increasing the thermal transfer between a patient and the second thermal-exchange fluid disposed within the fluid containment layer 803. Specifically, it has been found that welding of the patient interface layer 850 to the projections 854 on the bottom surface of the intermediate 840 layer can result in sagging of the patient interface layer 850 between adjacent projections. That is, the heat of the RF welding can result in permanent deflection of the patient interface layer 850. Accordingly, when adhesive material is applied to such a deformed patient interface layer 850, an air gap 870 can be formed between the patient interface layer 850 and the applied adhesive 816. See FIG. 9G. Such an air gap 870 acts as insulation and reduces the transfer of heat between the second thermal-exchange fluid contained in the chambers 832 of the fluid containment layer 830 when the pad 800 is adhered to a patient. In contrast, when the patient interface layer is secured to the intermediate layer by peripheral attachment, or at less that all locations within the perimeter, the patient interface layer is non-deformed (e.g., substantially planar) and fewer or no air gaps exist between it and the adhesive. See, e.g., FIG. 9B.

Figure 10A:
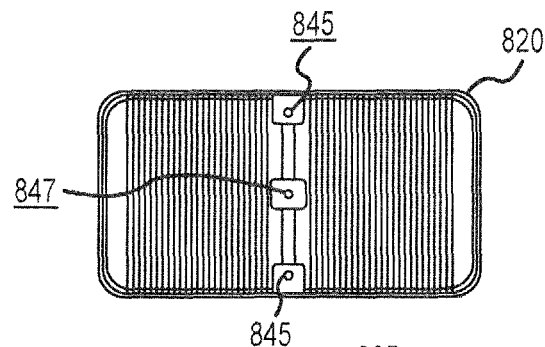
FIGS. 10A, 10B, and 10C are top views of adjacent layers comprising the medical pad embodiment of FIG. 9A.
Figure 10B:
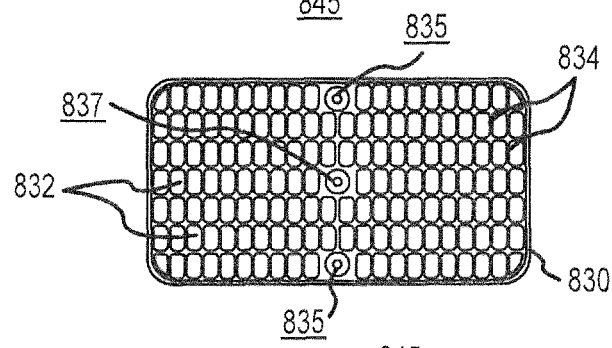
Figure 10C:
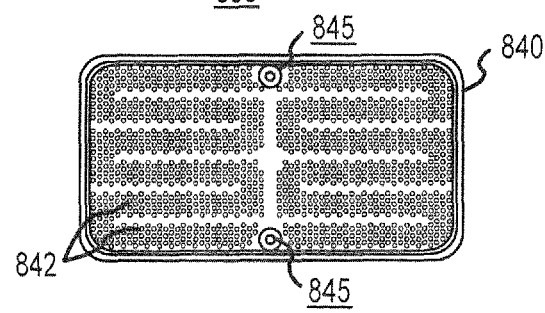
Figure 10D:
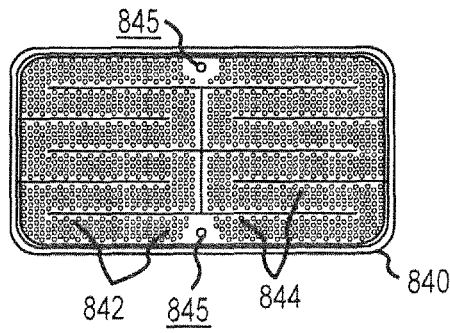
FIG. 10D is a bottom view of the layer of the medical pad embodiment of FIG. 8 that is shown in FIG. 10C.

In relation to the above-noted features, reference is now also made to FIGS. 10A, 10B, and 10C, which illustrate top views of layers 820, 830 and 840, and FIG. 10D which illustrates a bottom view of layer 840. Top layer 820 may define widthwise pleats, different ones of which may be positionable between columns of chambers 832 of containment layer 830. Top layer 820 may also include openings 825 for positioning of inlet port 802a and outlet port 802b therethrough.

As may be appreciated, the inlet port 802a and outlet port 802b may extend through aligned openings in the top layer 820, containment layer 830, and intermediate layer 840 to provide fluid communication with the circulation layer defined by intermediate layer 840 and fluid interface layer 850. Further, top layer 820 may include one or more opening(s) 827 for receipt of a fill port 804 therethrough, as shown in FIG. 9A, for selective use in flowing a second thermal-exchange fluid into the containment layer (e.g., during assembly of medical pad 800).

Reference is now made to FIG. 10B which illustrates containment layer 830 with chambers 832 and indentations 834 defining a matrix of rows and columns. Further, containment layer 830 may include openings 835 for positioning inlet port 802a and outlet port 802b therethrough. Additionally, containment layer 830 may include one or more opening(s) 837 for receipt of fill port 804 therethrough, as shown in FIG. 9A.

As illustrated in FIGS. 10C and 10D, intermediate layer 840 may also include openings 845 for positioning inlet port 802a and outlet port 802b therethrough. Additionally, intermediate layer 840 may include one or more opening(s) 847 for receipt of fill port 804 therethrough, as shown in FIG. 9A.

In relation to FIG. 10C, depressions 842 are shown on the top side of the intermediate layer 840. In relation to FIG. 10D, such depressions 842 define downward projections on the bottom side of the intermediate layer 840. Additionally, ribs 844 are provided that project downward on the bottom side of the intermediate layer 840. In turn, tortuous flow paths may be defined for the flow of a first thermal-exchange fluid between ribs 844, around the projections defined by depressions 842. As may be appreciated, such tortuous fluid flow may occur between inlet port 802a and outlet port 802b.

Figure 11A:
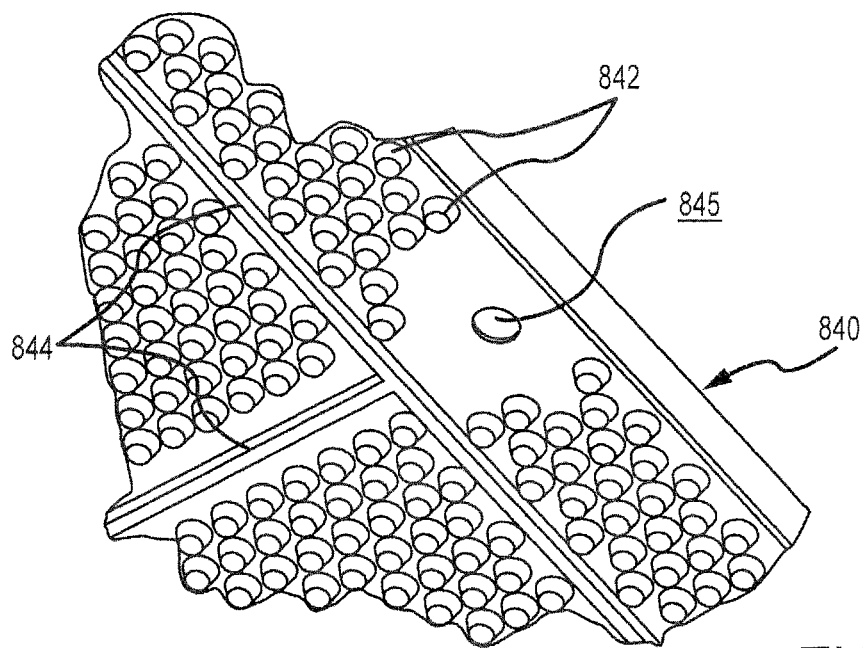
FIGS. 11A and 11B are bottom views of a cut-away, side portion of the layer of the medical pad embodiment of FIG. 8 that is shown in FIGS. 10C and 10D.

In this regard, reference is now made to FIGS. 11A and 11B, and FIGS. 12A and 12B. FIG. 11A illustrates a cutaway portion of a bottom side a side edge portion of intermediate layer 840, showing an opening 845 extending therethrough, and illustrating projections, corresponding with depressions 842 and ribs 844 projecting downward on the bottom side of the intermediate layer 840. As shown, depressions 842 are of an inverted, frusto-conical configuration.

Figure 11B:
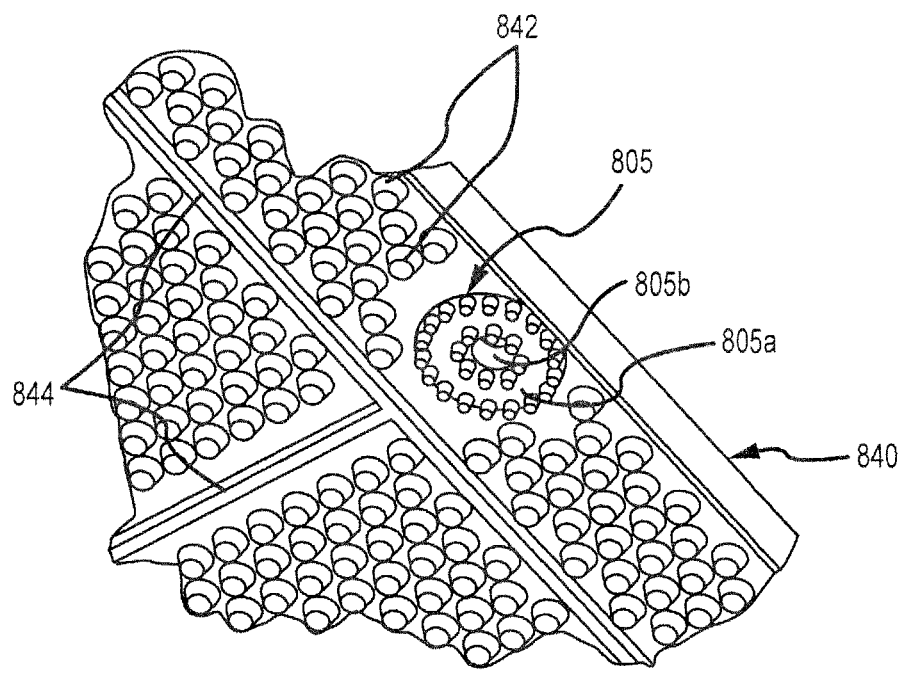

FIG. 11B illustrates the cutaway portion shown in FIG. 11A with an enlarged end 805 of inlet port 802a disposed on a bottom side of intermediate layer 840. As shown, enlarged end 805 includes a disk portion 805a, an aperture 805b and stand-off members 805c projecting away from disk portion 805a about aperture 805b. Inlet port 802a may be of a sufficiently rigid construction (e.g., comprising an integral, molded plastic material), such that stand-off members 805c maintain a desired layer-to-layer spacing for fluid flow at aperture 805b.

Figure 12A:
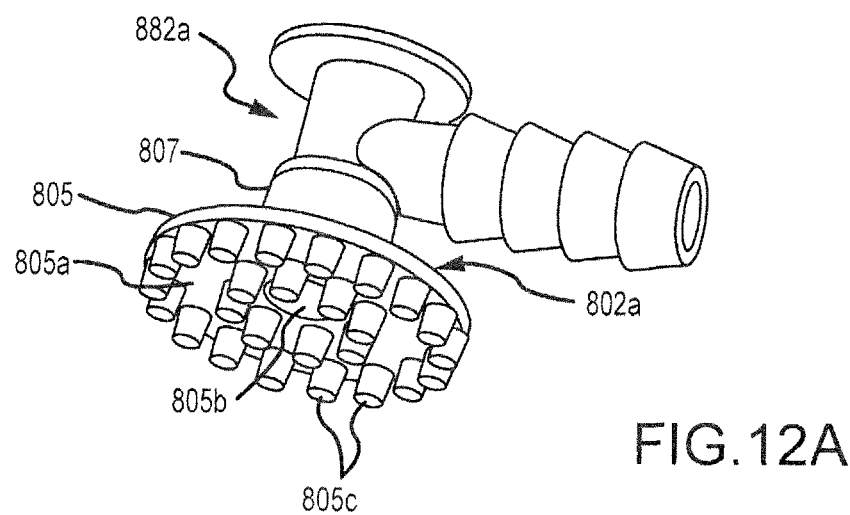
FIGS. 12A and 12B comprise a perspective view, and a cross-sectional perspective view, respectively, of an inlet port of the medical pad embodiment shown in FIG. 8 interconnected to a connector of a fluid circulation line illustrated in FIG. 8.
Figure 12B:
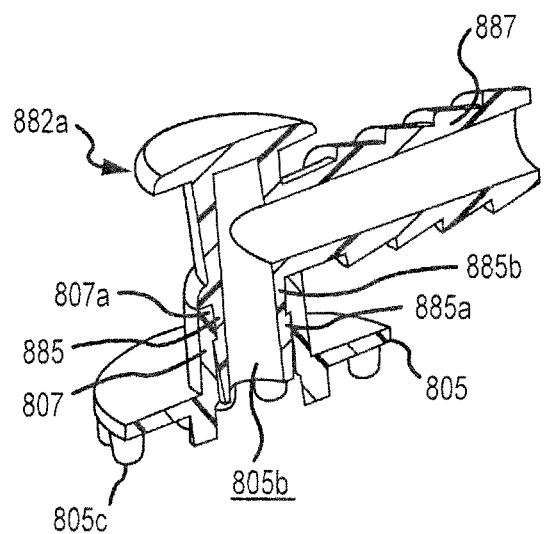

Inlet port 802a is shown interconnected to a connector 882a in FIGS. 12A and 12B. As illustrated, in addition to the enlarged end 805, inlet port 802a comprises a tubular portion 807 in fluid communication with aperture 805b. As may be appreciated, tubular portion 807 may be sized to fit through openings 825, 835, and 845 of the top layer 820, containment layer 830, and intermediate layer 840, respectively. Further, tubular portion 807 may be configured for selective interconnection with connector 882a.

For example, and as shown in FIG. 12B, tubular portion 807 may be configured together with connector 882a for one-way, snap-fit interconnection. For such purposes, a top end of tubular portion 807 may be sized to receive a tubular port 885 at connector 882a. Further, tubular portion may be provided with an inwardly protruding lip 807a. In turn, first tubular port 885 may have a tapered end portion 885a and adjacent recess 885b for snap-fit receipt of the lip 807a of the tubular portion 807 of the inlet port 802a. As further shown in FIGS. 12A and 12B, connector 882a may be of an L-shaped configuration that includes first and second tubular ports 885 and 887, adjoined at elbow 886, thereby yielding a low-profile interconnection footprint. Tubular part 887 may be barbed for retentive, fluid-type interconnection with tubing comprising fluid circulation line 880a. As may be appreciated, outlet port 802b and connector 882b may be configured in a manner analogous to inlet port 802a and connector 882a described above, respectively.

Figure 13A:
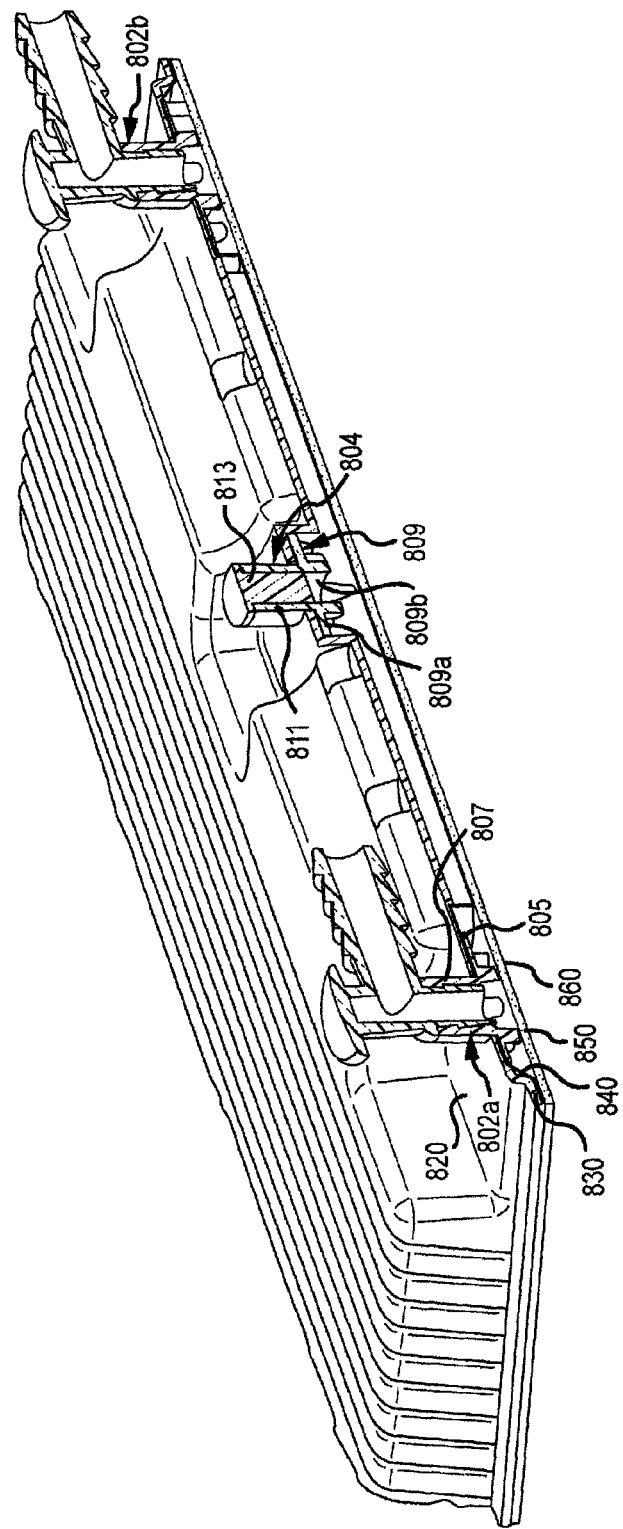
FIGS. 13A and 13B illustrate offset, widthwise, cross-sectional views of the medical pad embodiment shown in FIG. 8.
Figure 13B:
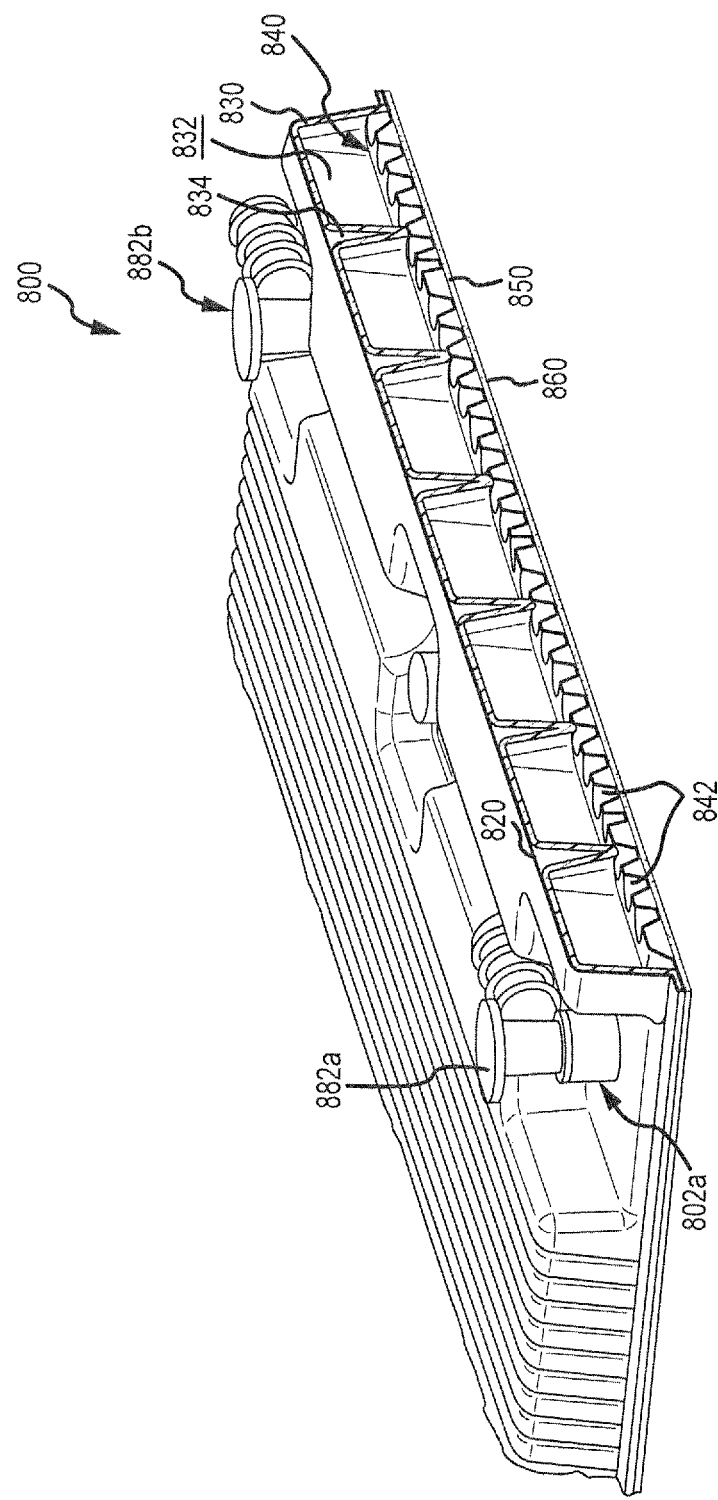

Reference is now made to FIGS. 13A and 13B which illustrate cross-sectional views of medical pad 800, with inlet port 802a and outlet port 802b thereof interconnected to connectors 882a and 882b, respectively. Fluid circulation lines 880a and 880b are not shown to facilitate discussion.

As shown in FIG. 13A, the enlarged ends 805 of inlet port 802a and outlet port 802b are positioned between fluid interface layer 850 and intermediate layer 840 to provide for a first thermal-exchange fluid flow in to and out of the circulation layer defined by interface layer 850 and intermediate layer 840. As noted, the stand-off members 805b maintain a minimum desired spacing to facilitate fluid flow in to and out of the fluid circulation layer. As further shown by FIG. 13A, fill port 804 may comprise and enlarged end 809 disposed between a bottom side of containment layer 830 and the top side of intermediate layer 840. The enlarged end 809 may include a disk portion 809a, an aperture 809b and stand-off members 809c projecting away from disk portion 809a about aperture 809b. The stand-off members 809c maintain a minimum desired spacing to facilitate fluid flow into the containment layer. The fill port 804 further includes tubular portion 811 for selective fluid interconnection to and disconnection from a source of the second thermal-exchange fluid during filling of the containment layer. A plug 813 may be provided to close-off tubular portion 811 after filling of the containment layer.

As may be appreciated, medical pad 800 may be readily assembled and readied for use. For example, interface layer 850 may be provided with a removable layer 860 removably attached to the bottom adhesive surface of the fluid interface layer. In turn, the top side of the fluid interface layer 850 may be interconnected to a bottom side of the intermediate layer 840 with enlarged ends 805 of ports 802a and 802b positioned therebetween, and tubular portions 807 located through openings 845, 835, and 825. Such interconnection may occur subsequent to or prior to interconnection of the top layer 820, containment layer 830, and intermediate layer 840 about the peripheries thereof. As may be appreciated, the enlarged end 809 of fill port 804 may be disposed between intermediate layer 840 and containment layer, with tubular portion positioned through openings 847, 837, and 827, prior to such interconnection.

Relatedly, prior to use, the second thermal-exchange fluid may be flowed through fill port 804 into the containment layer defined by containment layer 830 and intermediate layer 840. In this regard, the second thermal-exchange fluid may be introduced in a manner so that it flows through fill port 804, depressions 842 and in between the bottom side of containment layer 830 and top side of intermediate layer 840 to fill depressions 842 and at least a portion of the chambers 832 across the lateral entirety of the containment layer.

In one example, a vacuum may be initially established in the containment layer via use of fill port 804. In turn, fill port 804 may be interconnected to a source for the second thermal-exchange fluid. In one approach, a gel material (e.g., a cellulose gel comprising CMC, water and a cross-linking material such as aluminum acetate) may be employed. The gel may be flowed into the containment layer to fill depressions 842 and at least a portion of or substantially all of the volumes of chambers 832. Plug 813 may then be retainably introducing in fill port 804. In turn, the gel material may be allowed to cure, wherein cross-linking occurs so that gel material sets to maintain a shape defined by the volume of containment layer.

Figure 14A:
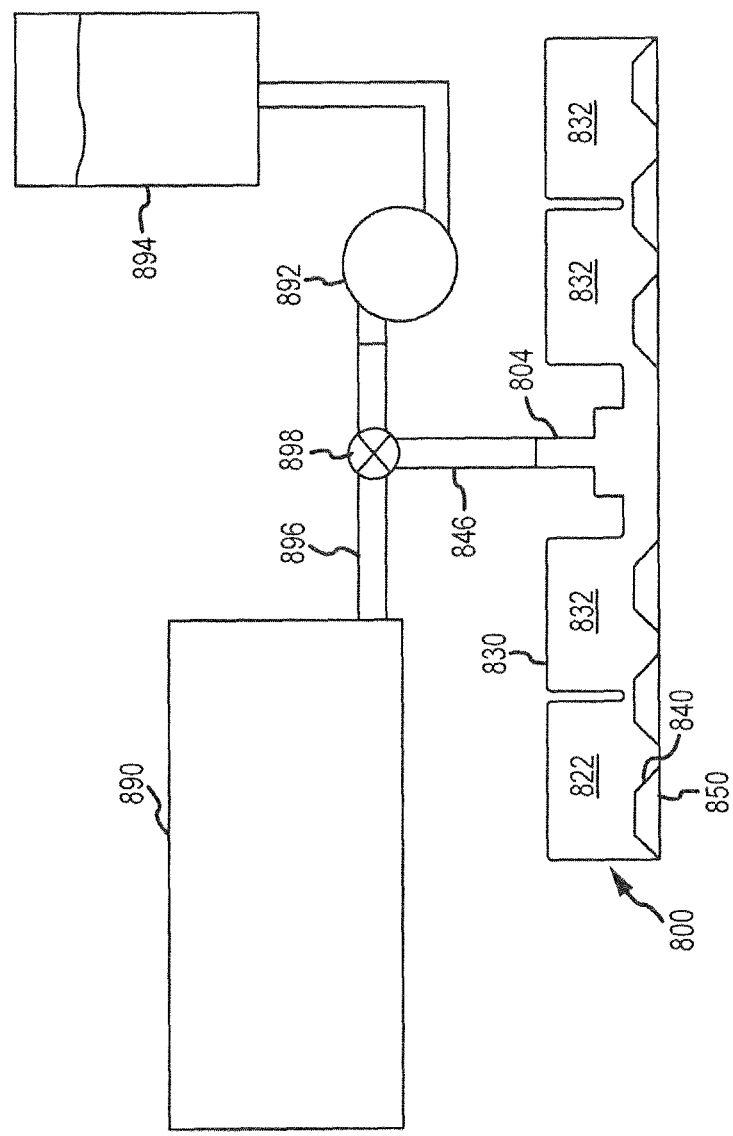
FIGS. 14A and 14B illustrate two systems for introducing a gel material into a fluid containment layer of a medical pad.
Figure 14B:
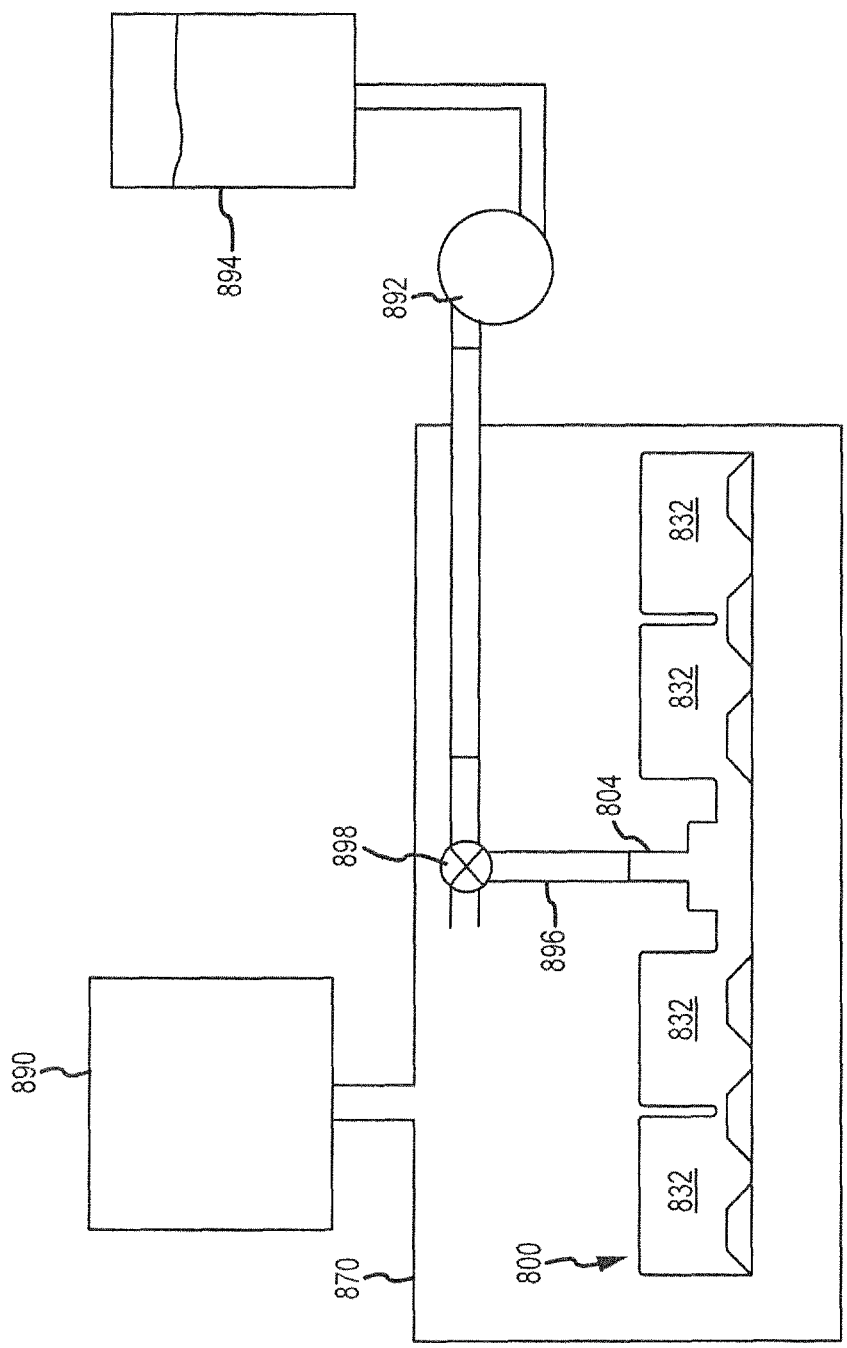

FIGS. 14A and 14B illustrate two exemplary systems for use flowing the second thermal-exchange fluid into the containment layer 830. As shown in FIG. 14A, the second thermal-exchange fluid may be flowed into the containment layer of the medical pad 800 and utilizing a vacuum source 890 and a pump 892 connected to a reservoir 894 including a supply of the thermal-exchange fluid. More specifically, the vacuum source 890 may be interconnected to the fill port 804 of the medical pad utilizing one or more connector tubes 896. Once connected to the medical pad 800, the vacuum source 890 may be operated to reduce pressure within the chambers 832 of the containment layer 830 to a pressure that is below atmospheric pressure. In one arrangement, the vacuum source 890 is operative to evacuate the containment layer to a pressure below 100 mmHg (e.g., 100 Torr). In a further arrangement, the vacuum source 890 is operative to evacuate the containment layer to a pressure below 10 mmHg (e.g., 10 Torr) and more preferably to or below 1 mmHg (e.g., 1 Torr). That is, the inventors have found that significantly reducing the internal pressure of the containment layer 830 relative to atmospheric pressure results in a more even fill of the thermal-exchange fluid into the chambers 832 of the containment layer 830. Once a desired pressure level (e.g., vacuum) is achieved within the containment layer, a valve 898 disposed within the tubing 896 between the vacuum source and the inlet port 804 of the medical pad 800 may be closed to isolate the vacuum source 890 from the fluid containment layer 830 of the medical pad 800. Furthermore, the valve 898 may connect a source (e.g., reservoir) of the thermal-exchange fluid to the inlet port 804. In order to flow the generally viscous thermal-exchange fluid into the chambers 832 of the containment layer 830, it is typically necessary to incorporate a pump 892 between the reservoir 894 and the medical pad 800. In this regard, the pump 892 is operative to pump the thermal-exchange fluid under positive pressure into the chambers of the fluid containment layer 830. Evacuation of the air from the fluid containment layer 830 allows for pumping the thermal-exchange fluid into the chambers of the fluid containment layer with little or no residual air remaining within the chambers 832.

In a further arrangement, the fluid circulation layer (e.g., fluid flow channels) defined by the interface layer 850 and intermediate layer 840 may likewise be evacuated to a pressure below atmospheric pressure (not shown) prior to flowing the thermal-exchange fluid into the chambers 832 of the fluid containment layer 830. Such evacuation of the fluid circulation layer prevents the pad 800 from the deforming during the evacuation of the fluid containment layer 830. That is, as both layers are at an equal pressure, the pad 800 does not warp due to the pressure difference between the layers. This likewise allows for more even filling of the chambers 832 of the fluid containment layer 830.

In a further arrangement, the entire medical pad 800 may be disposed within a vacuum chamber 870 to affect evacuation of both the fluid containment layer and the fluid circulation layer. See FIG. 14B. In this embodiment, rather than attaching the port 804 directly to the vacuum source 890, the port 804 may initially be vented to the interior of the vacuum chamber 870. Again, when desired internal pressure is achieved within the fluid containment layer and the fluid circulation layer, the valve 898 may be moved to isolate the fluid containment layer 830 from the vacuum chamber and open the fluid containment layer to the thermal-exchange fluid in the reservoir 894. As will be appreciated, this embodiment allows for simultaneously evacuating both layers of the medical pad 800.

After the thermal-exchange fluid is flowed into the chambers 832 of the fluid containment layer 830, adhesive material may be applied to the bottom of the patient interface layer 850. That is, the adhesive (e.g., hydrogel material) may be applied to the bottom surface of the patient interface layer while the pad is maintained in the vacuum chamber below atmospheric pressure. Such application in below atmospheric conditions may allow for applying the adhesive substantially free of air pockets between the adhesive and the sheet-like material that forms the bottom surface of the pad 800.

Figure 15:
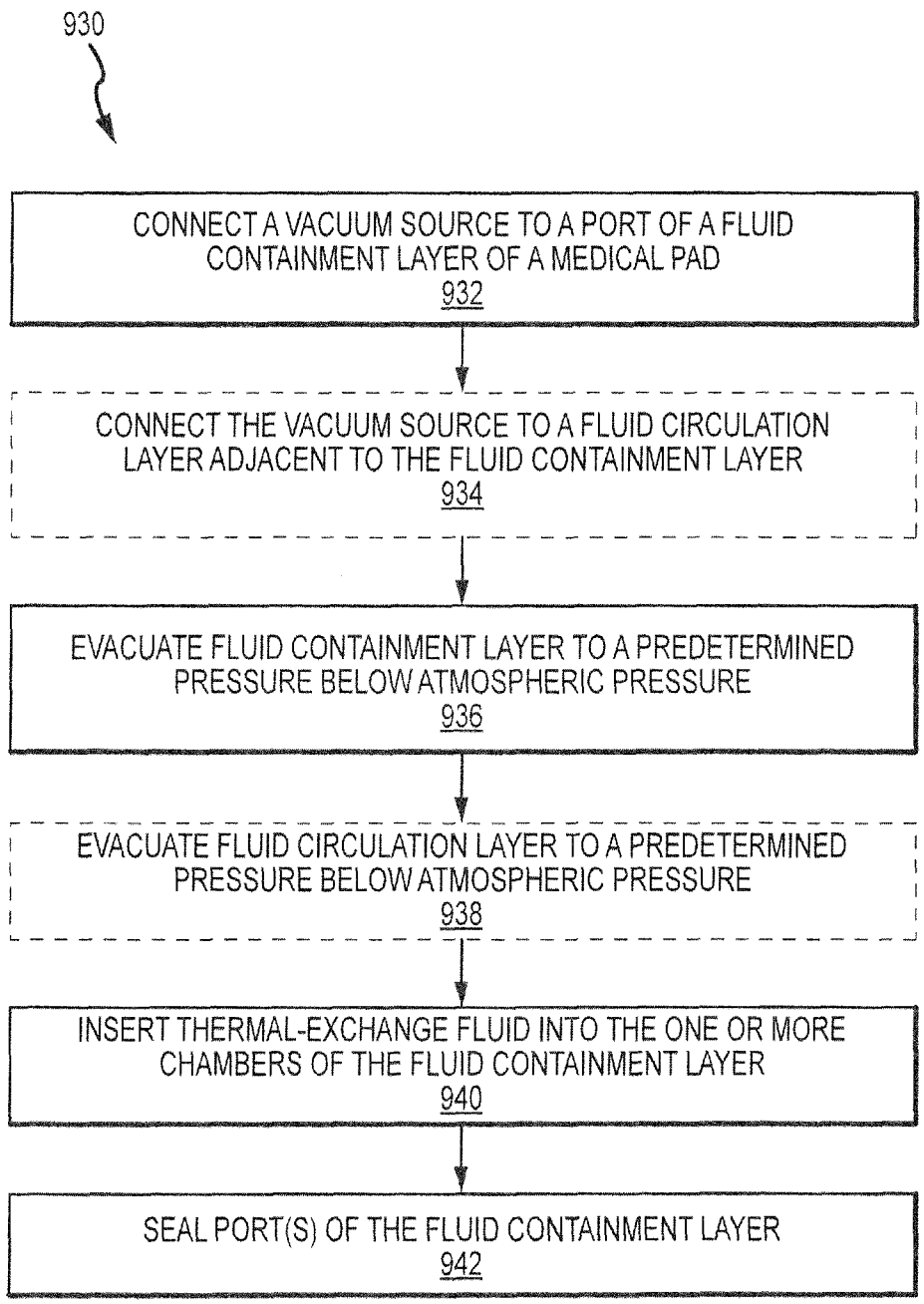
FIG. 15 is a flow diagram of a process for introducing a gel material into a fluid containment layer of a medical pad.

FIG. 15 illustrates a flow diagram of the process (930) for filling a fluid containment layer 830 of a medical pad 800. Initially, a vacuum source is connected (932) to the port of a fluid containment layer of a medical pad. Optionally, the vacuum source may also be connected (934) to a fluid circulation layer that is adjacent to the fluid containment layer. As noted above, connection between the fluid containment layer and or fluid circulation layer may be by way of direct connection (e.g., via connecting tubes) or by way disposition of the medical pad into a vacuum chamber. Once connected to the vacuum source, the vacuum source may be operated to evacuate (936) the fluid containment layer and, in some embodiments, evacuate (938) the fluid circulation layer to a predetermined pressure below atmospheric pressure. Once the fluid containment layer is evacuated, a thermal-exchange fluid may be introduced (940) into the fluid containment layer. Once a predetermined amount of the thermal-exchange fluid is introduced into the fluid containment layer, a port connected to the vacuum source and or a source of the thermal-exchange fluid may be sealed (942) to maintain the fluid exchange-material within the fluid containment layer where the thermal-exchange fluid may cure into a gel material.

While introduction of the thermal-exchange fluid under vacuum allows for evenly filling the chambers 832 of the fluid containment layer 830 with little or no residual air within the chambers, this process requires specialized preparation of the thermal-exchange fluid. More specifically, the inventors have recognized that flowing of the thermal-exchange fluid at pressures beneath atmospheric pressures can result in the formation of bubbles within the thermal-exchange. That is, the liquid (e.g., water) utilized prepare the thermal-exchange fluid typically includes gases that are released at pressures below atmospheric pressure. If these gases are not removed from the water utilized to form the thermal-exchange fluid, bubbles form within the fluid during the filling process outlined above. Furthermore, it will be appreciated that such air bubbles provide significant resistance to thermal exchange and thus reduce the overall effectiveness of the second thermal-exchange fluid contained within the fluid containment layer 830. Accordingly, the inventors have recognized the need to de-gas the water utilized to form the thermal-exchange fluid prior to mixing the water with the other components that form the thermal-exchange fluid.

Figure 16:
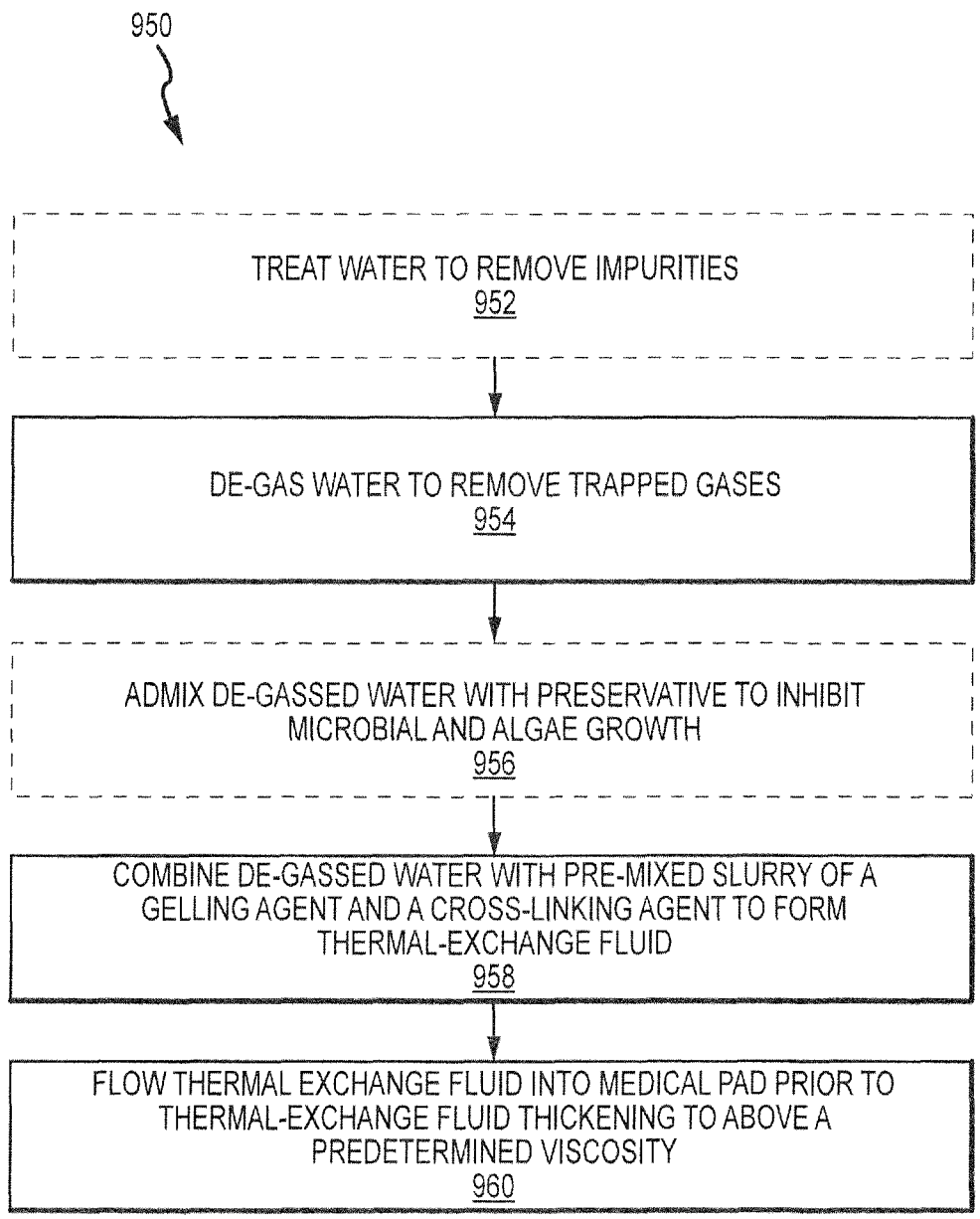
FIG. 16 illustrates a flow diagram of a process for preparing a thermal-exchange fluid.

FIG. 16 illustrates a process (950) for preparing the thermal-exchange fluid. Initially, tap water may be treated (952) by passing through a reverse osmosis treatment system to remove impurities from the water. Once the water is purified or otherwise treated, the water is de-gassed (954). Such de-gassing may be performed by pumping the water through a vacuum de-gassing system. Vacuum de-gassing is the process of using vacuum to remove trapped gases from liquids which can become entrapped when mixing the liquid with other components. If not removed before mixture, gas bubbles may form in the resulting mixture. This is especially evident in the current application where the resulting mixture is flowed into a fluid containment layer of a medical pad that is at a pressure below atmospheric pressure. In one embodiment, the treated water is pumped through a de-gassing canister that includes a gas permeable membrane that separates the liquid flow path (e.g., water flow path) from a gas chamber, which is maintained at vacuum. The process allows dissolved $O_2$, $CO_2$ and other gasses to disperse from the purified water resulting in a de-gassed water that is stored in a reservoir. One exemplary de-gassing system is the Liqui-Cell® Membrane Contactors marketed by Membrana, a division of Celgard, LLC, 13800 South Lakes Drive, Charlotte, N.C., 28273. The purified and de-gassed water is then preferably admixed (956) with a preservative such as potassium sorbate to inhibit growth of microbes or algae within the resulting thermal-exchange fluid. The water and preservative is then combined (958) with a pre-mixed slurry of a gelling agent and a cross-linking agent and in some instances a wetting agent (e.g., propane-diol) and/or a cross-linking accelerant (e.g., fumaric acid). In a preferred embodiment, the gelling agent is a carboxymethyl cellulose gel that may be utilized with an aluminum acetate cross-linking agent. This particular mixture is non-toxic and therefore well adapted for use in medical applications. However, it will be appreciated that the disclosed process is not limited to this particular formulation. The de-gassed water, preservative and pre-mixed slurry are, in one embodiment, combined (958) a vortex mixer to rapidly and fully wet the gelling agent. Once mixed, the resulting thermal-exchange fluid is in an initial fluid state though the cross-linking agent begins reacting with the gelling agent and forming a gel. However, the initial fluid remains in a non-gel state for a period of time that allows for flowing (960) the material into a medical pad prior to the fluid setting. That is, the thermal-exchange fluid may be introduced into a medical pad prior to the viscosity of the thermal-exchange fluid raises above a predetermined threshold due to cross-linking of the wetted gelling agent and cross-linking agent.

The present inventors have further recognized that the initial fluid characteristics of the pre-set thermal-exchange fluid are important to the flowing of the material into the medical pad. Specifically, the inventors have recognized that the initial viscosity of the fluid must be below a certain threshold to allow for fully and evenly filling the chambers of the fluid containment layer. Further, the initial viscosity of the thermal-exchange fluid is dependent upon the amount (e.g., by weight) of the gelling material utilized to form the thermal-exchange fluid. In this regard, an upper limit exists for the percentage by weight of the gelling agent that may be utilized. Likewise, the inventors have also recognized that a lower limit exists for the percentage by weigh of the gelling agent that will result in the thermal-exchange fluid setting into a gel. In this regard, there exists a narrow band of acceptable mixture concentrations that will provide the necessary characteristics for the thermal-exchange fluid; too much gelling agent results in an overly viscous fluid that does not fill the chambers of the fluid containment layer; too little gelling agent results in a thermal-exchange fluid that does not set up in a gel. Specifically, it has been determined that the initial viscosity be below 15,000 centipoise, more preferably below 10,000 centipoise and most preferably below 5,000 centipoise is required to effectively fill the fluid containment layer. Above the maximum threshold, the thermal-exchange fluid exhibits non Newtonian flow characteristics which makes even and complete flowing of the thermal-exchange fluid into the chambers of the fluid containment layer difficult or impractical. As will be appreciated, the viscosity ranges temperature dependent. Stated otherwise, an overly viscous thermal-exchange fluid (e.g., 20,000 centipoise at standard ambient conditions) may be heated to reduce its viscosity to an acceptable level. What is important is that the thermal-exchange fluid has the desired viscosity at the time of flowing/filling. Further, it has been recognized that an increase in the percentage concentration of a gelling agent lowers the overall thermal capacity of the resulting gel material. Therefore, it may be desirable to utilize a high molecular weight gelling agent, which allows for providing desired properties (e.g., viscosity, and gelling) in lower concentrations.

One exemplary embodiment of a formulation that provides the necessary initial viscosity for the thermal-exchange fluid and which allows for the thermal-exchange fluid to set into a semi-solid gel utilizes a carboxymethyl cellulose material (CMC) with a cross linking agent. Specifically, a concentration of between 0.5% and 3.5% by weight of carboxylethlycellulose weight and/or with a molecular weight between about 250,000-700,000 grams per mol and 0.1% and 0.4% by of a cross-linking agent(s) with water has been found to provide the necessary properties for the thermal-exchange fluid. In one specific embodiment, the cross-linking agent is an aluminum acetate material. To generate approximately 100 g of gel one specific formulation utilizes a solution of 100 ml of treated water (e.g., reverse osmosis treated and/or de-gassed), 0.14 g of potassium sorbate (an anti-microbial) that is combined with a slurry of 1 g of carboxymethyl cellulose, 0.15 g of aluminum acetate (cross-linking agent), 0.18 g of fumaric Acid: 0.18 g (gel formation accelerant) and 5 ml of propanediol (wetting agent).

In contemplated arrangements, after filling the fluid containment layer with the second thermal-exchange fluid, the medical pad 800 may be cooled. By way of example, in some embodiments, medical pad may simply be disposed in a freezer, yielding the medical pad 800 ready for use.

At the time of use bottom layer 860 may be removed from an adhesive surface on the bottom side of the fluid interface layer 850, and the adhesive surface of medical pad 800 may be contacted with a patient to initiate patient cooling. As may be appreciated, such patient cooling provides for thermal exchange between the second thermal-exchange fluid and the patient. Such thermal exchange may occur, for example, during transport of a patient.

Further, as and when patient cooling is desired via thermal exchange between a first thermal-exchange fluid circulated through medical pad 800 and a patient, connectors 882a, 882b of fluid circulation lines 880a, 880b may be interconnected to ports 802a, 802b, and connector 884 may be interconnected to a fluid circulation control system, wherein the first thermal-exchange fluid may be circulated through circulation layer of medical pad 800 to achieve patient cooling in tandem with or independent from patient cooling via the second thermal-exchange fluid (e.g., during and after the second thermal-exchange fluid warms).

The foregoing description of the present invention has been presented for purposes of illustration and description. Furthermore, the description is not intended to limit the invention to the form disclosed herein. Consequently, variations and modifications commensurate with the above teachings, and skill and knowledge of the relevant art, are within the scope of the present invention. The embodiments described hereinabove are further intended to explain known modes of practicing the invention and to enable others skilled in the art to utilize the invention in such or other embodiments and with various modifications required by the particular application(s) or use(s) of the present invention. It is intended that the appended claims be construed to include alternative embodiments to the extent permitted by the prior art.

Having described several embodiments, it will be recognized by those of skill in the art that various modifications, alternative constructions, and equivalents may be used without departing from the spirit of the invention. Accordingly, the above description should not be taken as limiting the scope of the invention, which is defined in the following claims.

What is claimed is:

1. A medical pad comprising:
   an upper containment sheet layer;
   an intermediate sheet layer having a plurality of depressions formed in a top surface defining a corresponding plurality of projections on a bottom surface; and
   a lower patient interface sheet layer having a top surface juxtaposed against the plurality of projections of the bottom surface of the intermediate sheet layer, wherein peripheries of the lower patient interface sheet layer and the intermediate sheet layer are connected such that spaces between the plurality of projections and the lower patient interface sheet layer collectively define a fluid circulation layer for containing a first thermal-exchange fluid circulatable therethrough; and
   wherein the upper containment sheet layer is disposed over the top surface of the intermediate sheet layer and peripheries of the upper containment sheet layer and the intermediate sheet layer are interconnected to define a fluid containment layer enclosing a second thermal-exchange fluid.

2. The medical pad of claim 1, wherein the upper containment sheet layer, intermediate sheet layer and lower patient interface sheet layer comprise polymer materials and the peripheries are welded.

3. The medical pad of claim 1, wherein each of the plurality of depressions have a substantially equal depth and each of the plurality of projections has a substantially equal height.

4. The medical pad of claim 3, wherein the top surface of the lower patient interface sheet layer is substantially planar.

5. The medical pad of claim 1, wherein at least some portions of the top surface of the lower patient interface sheet layer in contact with the plurality of projections are free of mechanical attachment thereto.

6. The medical pad of claim 1, wherein less than all portions of the top surface of the lower patient interface sheet in contact with the plurality of projections are fixedly attached thereto.

7. The medical pad of claim 1, wherein the intermediate sheet layer further comprises:
at least one elongated projection on the bottom surface of the intermediate sheet layer, wherein a portion of the top surface of the lower patient interface sheet layer is fixedly attached to the elongated projection.

8. The medical pad of claim 1, wherein a total area of the plurality of projections in contact with the lower patient interface sheet layer comprises at least 30% of a total area of the lower sheet layer.

9. The medical pad of claim 1, wherein a total area of the plurality of projections in contact with the lower patient interface sheet layer comprises at least 50% of a total area of the lower patient interface sheet layer.

10. The medical pad of claim 1, wherein the second thermal-exchange fluid has a freezing point of 0° C. or less.

11. The medical of claim 1, wherein the fluid containment layer extends across at least a majority of a lateral extent of the fluid circulation layer.

12. The medical pad of claim 1, wherein the upper containment sheet layer comprises a plurality of chambers for containing at least a portion of the second thermal exchange fluid therewithin.

13. The medical pad of claim 12, further comprising:
an insulative sheet layer extending over a top surface of the upper containment sheet layer and the plurality of chambers to insulate the plurality of chambers.

14. The medical pad of claim 12, wherein at least a portion of the plurality of chambers extends over at least a portion of the plurality of depressions, wherein the portion of the plurality of chambers is in fluid communication with the portion of the plurality of depressions.

15. The medical pad of claim 12, wherein each one of the plurality of chambers is in fluid communication with at least another adjacent one of the plurality of chambers.

16. The medical pad of claim 12, wherein the plurality of chambers comprise a plurality of enclosed chambers each enclosing a corresponding different portion of the second thermal-exchange fluid therewithin.

17. The medical pad of claim 12, wherein each of the plurality of chambers projects away from the top surface of the intermediate layer with indentations therebetween.

18. The medical pad of claim 17, wherein the plurality of chambers define a waffle shaped configuration.

19. The medical pad of claim 17, wherein at least a portion of the plurality of chambers are disposed in rows and columns, wherein the indentations extend between rows and columns.

20. The medical pad of claim 17, further comprising:
an insulative sheet layer extending over a top surface of the upper containment sheet layer and the plurality of chambers to insulate the chambers.

21. The medical pad of claim 20, wherein the insulative sheet layer further comprises:
a plurality of corrugations extending across a lateral extent thereof.

22. The medical pad of claim 20, wherein the insulative sheet further comprises:
at least one recess extending across a lateral extent thereof, wherein a bottom surface of the recess is disposed in an indentation between the chambers.

23. The medical pad of claim 22, wherein a depth of the recess extends over at least 20% of the depth of the indentation.

24. The medical pad of claim 22, wherein a depth of the recess extends over at least 50% of the depth of the indentation.

25. The medical pad of claim 1, further comprising an adhesive surface disposed on a bottom surface of the lower sheet layer and adapted for releasable adhesive contact with skin of a patient.

26. The medical pad of claim 25, wherein the adhesive surface comprises a hydrogel material.

27. The medical pad of claim 26, wherein the hydrogel material is applied to the bottom surface substantially free of air pockets between the bottom surface and the hydrogel material.

28. The medical pad of claim 25, wherein the fluid containment layer and the fluid circulation layer are adapted for conformal contact between the adhesive surface and the skin of the patient.

29. The medical pad of claim 1, further comprising:
a first port fluidly interconnected to the fluid circulation layer for circulating the first thermal exchange fluid into the fluid circulation layer; and
a second port fluidly interconnected to the fluid circulation layer for circulating the first thermal exchange fluid out of the fluid circulation layer.

30. The medical pad of claim 29, wherein the first port and the second port each extend away from the top surface of the intermediate sheet layer, through openings formed through the upper containment sheet layer.

31. The medical pad of claim 1, further comprising:
a port fluidly interconnected to the fluid containment layer for disposing the second thermal-exchange fluid into the fluid containment layer.

32. The medical pad recited in claim 1, wherein the second thermal exchange fluid comprises a liquid in a gel material.

33. The medical pad recited in claim 32, wherein the gel material is shape holding.

34. The medical pad recited in claim 1, wherein at least one of the first thermal exchange fluid or the second thermal-exchange fluid has a thermal conductivity that exceeds 5.0 W/mK.

35. The medical pad recited in claim 34, wherein the at least one of the first thermal exchange fluid or the second thermal-exchange fluid comprises a liquid containing a material having a thermal conductivity that exceeds a thermal conductivity of the liquid by at least a factor of 100.

* * * * *

UNITED STATES PATENT AND TRADEMARK OFFICE
CERTIFICATE OF CORRECTION

PATENT NO. : 9,622,907 B2
APPLICATION NO. : 13/662026
DATED : April 18, 2017
INVENTOR(S) : Carson et al.

It is certified that error appears in the above-identified patent and that said Letters Patent is hereby corrected as shown below:

On the Title Page

Page 3 References Cited, U.S. Patent Documents, delete "3,283,602", and insert --8,283,602--

Signed and Sealed this
Fourteenth Day of August, 2018

Andrei Iancu
*Director of the United States Patent and Trademark Office*